United States Patent [19]

Enders et al.

[11] 4,194,008
[45] Mar. 18, 1980

[54] N-ARYL-N'-(CYCLO)-ALKYL-THIOUREAS AND THEIR USE AS AGENTS FOR COMBATING ANIMAL PESTS AND PLANT PESTS

[75] Inventors: Edgar Enders, Cologne; Wilhelm Stendel, Wuppertal; Ingeborg Hammann, Cologne, all of Fed. Rep. of Germany

[73] Assignee: Bayer Aktiengesellschaft, Leverkusen, Fed. Rep. of Germany

[21] Appl. No.: 827,902

[22] Filed: Aug. 25, 1977

[30] Foreign Application Priority Data

Sep. 3, 1976 [DE] Fed. Rep. of Germany ....... 2639748
Dec. 21, 1976 [DE] Fed. Rep. of Germany ....... 2657772
Jun. 18, 1977 [DE] Fed. Rep. of Germany ....... 2727416

[51] Int. Cl.$^2$ ...................... A01N 9/12; C07C 157/05
[52] U.S. Cl. .................................. 424/322; 260/552 R
[58] Field of Search ....................... 260/552 R; 424/322

[56] References Cited

U.S. PATENT DOCUMENTS

| 3,683,001 | 8/1972 | Knowles .................... 260/552 R X |
| 3,686,303 | 8/1972 | Knowles .................... 260/552 R X |
| 3,734,961 | 5/1973 | Englehart .................. 260/552 R X |
| 3,799,759 | 3/1974 | Martin et al. ............... 260/552 R X |
| 3,801,635 | 4/1974 | Duerr et al. ................ 260/552 R |
| 3,813,436 | 5/1974 | Duerr et al. ................ 260/552 R X |
| 3,927,087 | 12/1975 | Dürr et al. ................. 260/552 R |
| 4,079,144 | 3/1978 | Dürr et al. ................. 260/552 A X |
| 4,097,605 | 6/1978 | Fancher ..................... 260/552 R X |

FOREIGN PATENT DOCUMENTS

| 273290 | 9/1964 | Australia ............................ 260/552 R |
| 644892 | 7/1962 | Canada .............................. 260/552 R |

OTHER PUBLICATIONS

Walter et al., Justus Liebigs Ann. Chem. 1969, 722, pp. 56–59.
Holdsworth et al., CA 54:24550f (1960).
Monsanto Co., CA 71:101511p (1969).
Walter et al., CA 81:3242p (1974).
Walter et al., CA 71:90966n (1969).

*Primary Examiner*—Thomas A. Waltz
*Attorney, Agent, or Firm*—Sprung, Felfe, Horn, Lynch & Kramer

[57] ABSTRACT

N-Aryl-N'-(cyclo)-alkyl-thioureas of the formula

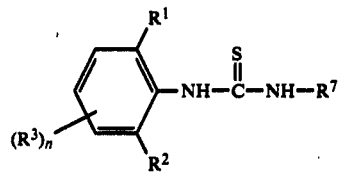

(I)

in which
  $R^1$ represents alkyl-($C_1$–$C_6$) or cycloalkyl-($C_3$–$C_7$),
  $R^2$ represents alkyl-($C_2$–$C_6$) or cycloalkyl-($C_3$–$C_7$),
  $R^3$ represents alkyl-($C_1$–$C_6$), alkenyl-($C_3$–$C_6$), cycloalkyl-($C_3$–$C_7$), cycloalkenyl-($C_5$–$C_7$) or halogen,
  n represents 0, 1 or 2, and
  $R^7$ represents optionally substituted cycloalkyl-($C_3$–$C_{10}$), optionally substituted cycloalkenyl-($C_5$–$C_{10}$) or the radical

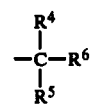

in which
  $R^4$ represents hydrogen, alkyl-($C_1$–$C_6$) or cycloalkyl-($C_3$–$C_7$) and
  $R^5$ and $R^6$ may be identical or different and represent alkyl-($C_1$–$C_6$) or cycloalkyl-($C_3$–$C_7$), and acid addition salts thereof, are useful for their ectoparasiticidal, insecticidal, fungicidal and acaricidal effects. These compounds may be produced, inter alia, by reacting aryl isothiocyanates of the formula

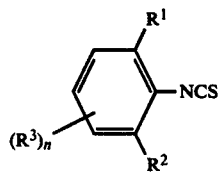

(II)

with amines of the formula $H_2N—R^7$.

12 Claims, No Drawings

N-ARYL-N'-(CYCLO)-ALKYL-THIOUREAS AND THEIR USE AS AGENTS FOR COMBATING ANIMAL PESTS AND PLANT PESTS

The present invention relates to new N-aryl-N'-(cyclo)-alkyl-thioureas, processes for their preparation and their use as agents for combating animal pests and plant pests, especially as ectoparasiticides, insecticides, fungicides and acaricides.

It has already been disclosed that N-aryl-N',N'-dialkyl-thioureas are active as ectoparasiticides, especially as tickicides against ticks of the genus boophilus (see, in this context, DT-OS (German Published Specification) No. 2,337,122).

Compared to the known and chemically related compounds, the N-aryl-N'-(cyclo)-alkyl-thioureas according to the invention show a better action against phosphoric acid ester-resistant ticks of the genus boophilus as well as a distinctly pronounced insecticidal side-effect, which is lacking in the comparative products from DT-OS (German Published Specification) No. 2,337,122. Furthermore, they are active, in agriculture, against insects which damage plants and against mites.

The present invention provides N-aryl-N'-(cyclo)-alkyl-thioureas of the general formula

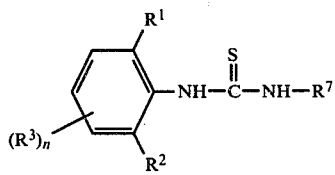

in which
R$^1$ represents alkyl-(C$_1$-C$_6$) or cycloalkyl-(C$_3$-C$_7$),
R$^2$ represents alkyl-(C$_2$-C$_6$) or cycloalkyl-(C$_3$-C$_7$),
R$^3$ represents alkyl-(C$_1$-C$_6$), alkenyl-(C$_3$-C$_6$), cycloalkyl-(C$_3$-C$_7$), cycloalkenyl-(C$_5$-C$_7$) or halogen,
n represents 0, 1 or 2, and
R$^7$ represents optionally substituted cycloalkyl-(C$_3$-C$_{10}$), optionally substituted cycloalkenyl-(C$_5$-C$_{10}$) or the radical

in which
R$^4$ represents hydrogen, alkyl-(C$_1$-C$_6$) or cycloalkyl-(C$_3$-C$_7$) and
R$^5$ and R$^6$ may be identical and represent alkyl-(C$_1$-C$_6$) or cycloalkyl-(C$_3$-C$_7$),
and acid addition salts thereof.

The compounds of the invention possess a powerful action against animal pests and plant pests, especially an ectoparasiticidal, insecticidal, fungicidal and acaricidal action.

More particularly, the invention provides a method of combating animal and plant pests which comprises applying to the pests, or a habitat thereof a compound according to the invention or in admixture with a diluent or carrier.

Further, it has been found that the new N-aryl-N'-(cyclo)-alkyl-thioureas of the formula (I) are obtained when
(a) aryl isothiocyanates of the formula

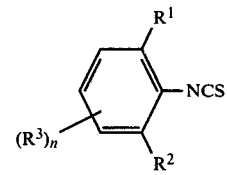

are reacted with amines of the formula

or alternatively
(b) isothiocyanates of the formula

are reacted with arylamines of the formula

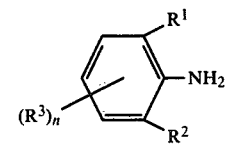

in which formulae
R$^1$, R$^2$, R$^3$, R$^7$ and n in each case have the abovementioned meaning.

In either case the compounds of the invention may be converted from the basic form into an acid addition salt by reaction with an organic or inorganic acid.

Surprisingly, the new N-aryl-N'-(cyclo)-alkyl-thioureas according to the invention show a more pronounced ectoparasiticidal action than the chemically closely related N-aryl-N',N'-dialkyl-thioureas from DT-OS (German Published Specification) No. 2,337,122 and additionally an insecticidal action as well as an action against mites, which are lacking in the compounds from DT-OS (German Published Specification) No. 2,337,122.

If, in accordance with variant (a), 2,6-di-sec.-butyl-phenyl isothiocyanate and tert.-butylamine are used as starting materials, the course of the reaction can be represented by the following equation:

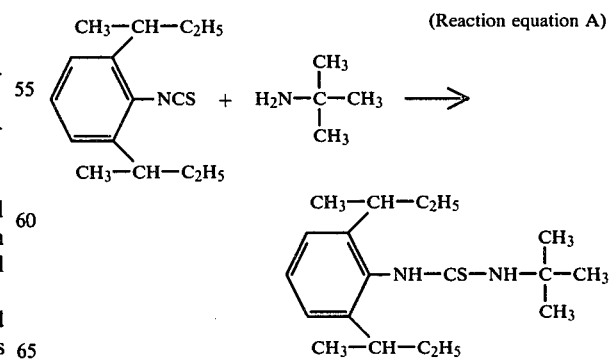

(Reaction equation A)

If, in accordance with variant (b), tert.-butyl isothiocyanate and 2,6-diisopropyl-aniline are used as the starting materials, the course of the reaction can be represented by the following equation:

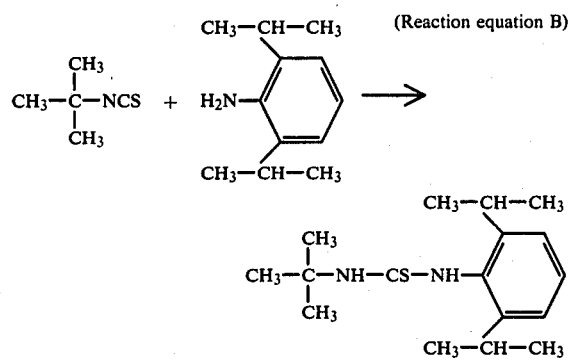

(Reaction equation B)

If, in accordance with variant (a), 2,6-di-sec.-butyl-phenyl isothiocyanate and cyclopentylamine are used as starting materials, the course of the reaction can be represented by the following equation:

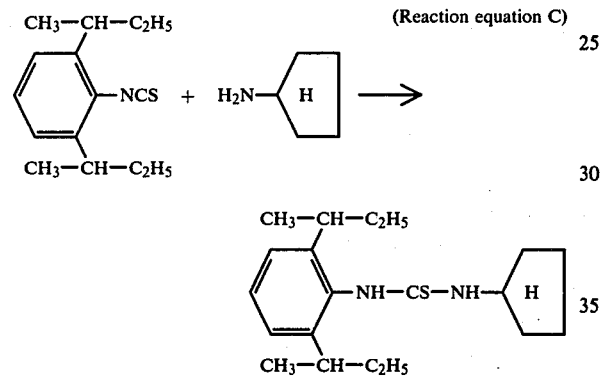

(Reaction equation C)

If, in accordance with process (b), cyclopentyl isothiocyanate and 2,6-di-sec.-butyl-aniline are used as starting materials, the course of the reaction can be represented by the following equation:

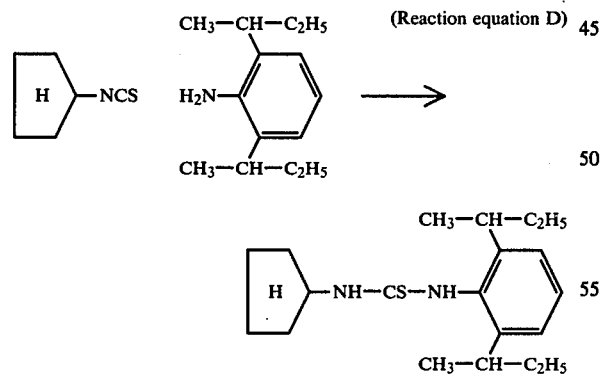

(Reaction equation D)

The following alkyl groups are preferred for the radicals $R^1$, $R^3$, $R^4$, $R^5$ and $R^6$: methyl, ethyl, propyl, isopropyl, butyl, sec.-butyl, isobutyl, tert.-butyl, pent-2-yl, pent-3-yl, tert.-pentyl or hex-2-yl; the following cycloalkyl groups are preferred for the radicals $R^1$, $R^2$, $R^3$, $R^4$, $R^5$ and $R^6$: cyclopropyl, cyclopentyl, cyclohexyl or cycloheptyl; chlorine, bromine and fluorine are preferred halogen atoms for the radical $R^3$, especially chlorine or bromine; and the following optionally substituted cycloalkyl-($C_3$-$C_{10}$) groups are preferred for $R^7$: cyclopropyl, 2-methyl-cyclopropyl, 1-ethyl-cyclopropyl, cyclobutyl, 1-methyl-cyclobutyl, 2-methyl-cyclobutyl, cyclopentyl, 1-methyl-cyclopentyl, 1-ethyl-cyclopentyl, 2-methyl-cyclopentyl, 3-methyl-cyclopentyl, cyclohexyl, 1-, 2-, 3- or 4-methyl-cyclohexyl, 2-, 3- or 4-trifluoromethyl-cyclohexyl, 2- or 4-ethyl-cyclohexyl, 2,4-, 2,6-, 2,5- or 3,5-dimethyl-cyclohexyl, 3,5-bis-trifluoromethyl-cyclohexyl, 4-methyl-3-trifluoromethyl-cyclohexyl, 2- or 4-isopropyl-cyclohexyl, 2,4- or 2,6-diethyl-cyclohexyl, cycloheptyl, cyclooctyl and 1-methyl-cyclooctyl.

The aryl isothiocyanates of the general formula (II) and (cyclo)alkyl isothiocyanates of the general formula (IV) used as starting compounds are known or can be manufactured in accordance with known methods, for example by reacting arylaines of the general formula (V) or (cyclo)alkylamines of the general formula (III) with thiophosgene, by reacting N-aryl- or N-(cyclo)alkyl-dithiocarboxylic acid salts with phosgene or oxidising agents, or from (cyclo)alkyl halides and alkali metal thiocyanates or from olefines and thiocyanic acid (see Houben-Weyl, "Methoden der organischen Chemie" ("Methods of Organic Chemistry"), Volume IX, pages 867–878).

The following may be mentioned as examples of starting compounds for the aryl isothiocyanates of the general formula (II) to be used according to reaction equation A: 2,6-dimethy-phenyl isothiocyanate, 2-methyl-6-ethyl-phenyl isothiocyanate, 2,6-diethyl-phenyl isothiocyanate, 2-ethyl-6-isopropyl-phenyl isothiocyanate, 2,6-diisopropyl-phenyl isothiocyanate, 2,6-di-sec.-butyl-phenyl isothiocyanate, 2-methyl-6-sec.-butyl-phenyl isothiocyanate, 2-ethyl-6-sec.-butyl-phenyl isothiocyanate, 2-isopropyl-6-sec.-butyl-phenyl isothiocyanate, 2-methyl-6-iso-propyl-phenyl isothiocyanate, 2-methyl-6-cyclopentyl-phenyl isothiocyanate, 2-ethyl-6-cyclopentyl-phenyl isothiocyanate, 2-isopropyl-6-cyclopentyl-phenyl isothiocyanate, 2,6-dicyclopentyl-phenyl isothiocyanate, 2-methyl-6-tert.-butyl-phenyl isothiocyanate, 2-ethyl-6-tert.-butyl-phenyl isothiocyanate, 2-methyl-6-cyclohexyl-phenyl isothiocyanate, 2-ethyl-6-cyclopentyl-phenyl isothiocyanate, 2,4-dimethyl-6-ethyl-phenyl isothiocyanate, 2,4-dimethyl-6-isopropyl-phenyl isothiocyanate, 2,4-dimethyl-6-sec.-butyl-phenyl isothiocyanate, 2,4-dimethyl-6-tert.-butyl-phenyl isothiocyanate, 2,4,6-trimethyl-phenyl isothiocyanate, 2,6-diethyl-4-methyl-phenyl isothiocyanate, 2,6-diisopropyl-4-methyl-phenyl isothiocyanate, 3,5-dimethyl-2,6-diethyl-phenyl isothiocyanate, 3-methyl-2,6-diethyl-phenyl isothiocyanate, 3-chloro-2,6-diethyl-phenyl isothiocyanate, 2,4,6-triisopropyl-phenyl isothiocyanate, 2,6-di-(pent-2-yl)-phenyl isothiocyanate, 2,4,6-triethyl-phenyl isothiocyanate, 2,6-diethyl-4-propyl-phenyl isothiocyanate, 2,6-diethyl-4-isopropyl-phenyl isothiocyanate, 2,6-diethyl-4-n-butyl-phenyl isothiocyanate, 2,6-diethyl-4-sec.-butyl-phenyl isothiocyanate, 2,6-diethyl-4-n-pentyl-phenyl isothiocyanate, 2,6-diethyl-4-cyclopentyl-phenyl isothiocyanate, 2,6-diethyl-4-pent-3-yl-phenyl isothiocyanate, 2,6-diethyl-4-(1,1-dimethyl-propyl)-phenyl isothiocyanate, 2,6-diethyl-4-(3-methyl-butyl)-phenyl isothiocyanate, 2,6-diethyl-4-[3-methyl-but-2-yl]-phenyl isothiocyanate, 2,6-diethyl-4-n-hexyl-phenyl isothiocyanate, 2,6-diethyl-4-allyl-phenyl isothiocyanate, 2,6-diethyl-4-crotyl-phenyl isothiocyanate, 2,6-diethyl-4-(2,2-dimethyl-vinyl)-phenyl isothiocyanate, 2,6-diethyl-4-hex-2-yl-phenyl isothiocyanate, 2,6-diethyl-4-hex-3-yl-phenyl isothiocyanate, 2,6-diethyl-4-(2,2-dimethylpropyl)-phenyl isothiocyanate, 2,6-diethyl-4-[4-methyl-pent-3-yl]-phenyl isothiocyanate, 2,6-diethyl-4-(2,3-dimethyl-butyl)-phenyl isothiocyanate, 2,6-diethyl-4-(2-ethyl-butyl)-phenyl isothiocyanate, 2,6-diethyl-4-(1-methyl-cyclopentyl)-phenyl isothiocyanate, 2,6-diethyl-4-4-cyclohexyl-phenyl isothiocyanate, 2,6-diethyl-4-cyclohex-1-enyl-phenyl isothiocyanate, 2,6-diethyl-4-(1-methyl-cyclohexyl)-phenyl isothiocyanate 2,6-diethyl-4-cycloheptyl-phenyl isothiocyanate, 2,6-diethyl-4-fluoro-phenyl isothiocyanate and 2,6-diethyl-3-fluoro-phenyl isothiocyanate.

The arylamines of the general formula (V) on which the abovementioned aryl isothiocyanates are based on alternatively be used for the preparation of the compounds of the general formula (I) in accordance with reaction equation (B).

The following may be mentioned as examples of (cyclo)alkyl isothiocyanates of the general formula IV: isopropyl isothiocyanate, sec.-butyl isothiocyanate, pent-2-yl isothiocyanate, hex-2-yl isothiocyanate, oct-2-yl isothiocyanate, 3-methyl-but-2-yl isothiocyanate, 3-methyl-pent-2-yl isothiocyanate, 4-methyl-pent-2-yl isothiocyanate, pent-3-yl isothiocyanate, 2-methyl-pent-3-yl isothiocyanate, 2,4-dimethyl-pent-3-yl iso-thiocyanate, hex-3-yl isothiocyanate, 2-methyl-hex-3-yl isothiocyanate, 3,3-dimethyl-but-2-yl isothiocyanate, 2,2-dimethyl-pent-3-yl isothiocyanate, 1-cyclopropyl-ethyl isothiocyanate, 1-cyclopentyl-ethyl isothiocyanate, tert.-butyl isothiocyanate, tert.-pentyl isothiocyanate, 3-methyl-pent-3-yl isothiocyanate, 3-ethyl-pent-3-yl isothiocyanate, 2-methyl-pent-2-yl isothiocyanate, 2-methyl-hex-2-yl isothiocyanate, 3-methyl-hex-3-yl isothiocyanate and 2-methyl-oct-2-yl isothiocyanate.

The (cyclo)alkylamines of the general formula (III) on which the abovementioned alkyl isothiocyanates are based can alternatively be used for the preparation of compounds of the general formula (I) analogously to reaction equation A.

Preferred possible optionally substituted cycloalkylamines and cycloalkenylamines of the general formula (III) are cycloalkylamines and cycloalkenylamines which are optionally substituted by alkyl-($C_1$–$C_4$), alkenyl-($C_2$–$C_6$), trifluoromethyl or amino. Examples which may be mentioned are: cyclopropylamine, 1-methyl-cyclopropylamine, 1-allyl-cyclopropyamine, 1-ethyl-cyclopropylamine, 2-methyl-cyclopropylamine, cyclobutylamine, 1-methyl-cyclobutylamine, cyclopentylamine, 1-methyl-cyclopentylamine, 1-ethyl-cyclopentylamin e, 2-methylcyclopentylamine, 3-methyl-cyclopentylamine, cyclopent-2-enylamine, cyclohexylamine, 1-, 2-, 3- or 4-methyl-cyclohexyl-amine, 2-, 3- or 4- trifluoromethyl-cyclohexylamine, 2- or 4-ethyl-cyclohexylamine, 2- or 4-isopropyl-cyclohexylamine, 4-n-propyl-cyclohexylamine, 4-n-butyl-cyclohexylamine, 2,4-, 2,6-, 2,5-, 3,4- or 3,5-dimethyl-cyclohexylamine, 3,5-bis-trifluoromethyl-cyclohexylamine, 4-methyl-3-trifluoromethyl-cyclohexylamine, 2,4- or 2,6-diethyl-cyclohexylamine, cycloheptylamine, cyclohex-2-enylamine, cyclooctylamine, 1-methyl-cyclooctylamine, 2-norbornylamine, decahydro-1-naphthylamine and 1-amine-adamantane.

The cycloalkyl isothiocyanates or cycloalkenyl isothiocyanates of the general formula (IV) which correspond to the abovementioned cycloalkyl or cycloalkenylamines can be used for the preparation of the compounds of the general formula (I) in accordance with reaction equation D.

According to the invention, as already mentioned above, (a) the substituted aryl isothiocyanates of the general formula (II) are reacted with the (cyclo)alkylamines of the general formula (III) or alternatively (b) (cyclo)alkyl isothiocyanates of the general formula (IV) are reacted with arylamines of the general formula (V).

The reaction is carried out in molar or approximately molar ratios, but it is possible to employ the more volatile or less valuable component in excess, for example in 5–50% excess. However, in a preferred embodiment it is also possible to employ, for example, the (cyclo)alkylamines of the general formula (III) in a large excess, namely 2–20 mols per mol of aryl isothiocyanate II. Accordingly, they serve at the same time as solvents for the resulting thioureas of the general formula (I) and can, after the reaction has taken place, be largely recovered by distillation. In carrying out the reaction according to equation A or B, tertiary organic bases can be added to accelerate the reaction. For example, the reaction is carried out at temperatures from 10° to 120° C., especially at 20° to 60° C. The reaction of the substituted aryl isothiocyanates of the general formula (II) with the (cyclo)-alkylamines of the general formula (III) or alternatively of the (cyclo)alkyl isothiocyanates (IV) with the arylamines of the formula (V) can be carried out without solvents in a melt, or with addition of a solvent and diluent. As such it is possible to use, for example, hydrocarbons or halogenohydrocarbons, such as petroleum ether, wash benzine, ligroin, cyclohexane, benzene, toluene, chlorobenzene, methylene chloride, chloroform and carbon tetrachloride, and water-soluble solvents such as methanol, ethanol, acetone, acetonitrile and dimethylformamide. If required, further inorganic bases or, as already mentioned earlier, organic bases, can be added to the batches as accelerators; examples of such bases are triethylamine, 1,4-diaza-bicyclo-[2,2,2]-octane (DABCO), 1,5-diaza-bicyclo-[4,3,0]-non-5-ene (DBN), 1,8-diaza-biyclo-[5,4,0]-undec-7-ene (DBU), potassium hydroxide, sodium hydroxide, sodium hydride and sodium oxide.

Depending on the starting compounds, the reactions may take place exothermically and must be kept under control by cooling depending on the magnitude of the exothermic effect and presence of diluents, or the reactions may have to be accelerated by heating, for example to temperatures of 40°–150° C., preferably 40° to 100° C., especially 50°–100° C. Accordingly, the reaction conditions are individually different and depend on the nature and amount of the starting materials employed and on the solvent used.

Working up takes place either by distilling off the solvent and recrystallising the reaction product or by pouring the mixture into water or dilute aqueous mineral acids, filtering and drying.

The compounds in the following list (List A) may be mentioned as new N-aryl-N'-alkyl-thioureas of the general formula (I):

List A

N(2,6-diiso-propyl-phenyl)-N'-tert.-butyl-thiourea of melting point 135°–137° C., N-(2,6-diisopropyl-phenyl)-N'-tert.-pentyl-thiourea of melting point 134°–135° C., N-(2,6-diisopropyl-phenyl)-N'-(1,1,2,2-tetramethyl-propyl)-thiourea of melting point 161°–162° C., N-(2,6-diethyl-phenyl)-N'-tert.-butyl-thiourea of melting point 98°–100° C., N-(2,6-diethyl-phenyl)-N'-tert.-pentyl-thiourea of melting point 85°–87° C., N-(2,6-di-sec.-butyl-phenyl)-N'-tert.-pentyl-thiourea of melting point 116°–118° C., N-(2,6-di-sec.-butyl-phenyl)-N'-tert.-butyl-thiourea of melting point 115°–117° C., N-(2,6-diethyl-phenyl)-N'-isopropyl-thiourea of melting point 108°–110° C., N-(2,6-diethyl-phenyl)-N'-sec.-butyl-thiourea of melting point 78°–80° C., N-(2,6-di-sec.-butyl-phenyl)-N'-isopropyl-thiourea of melting point 108°–111° C., N-(2,6-di-sec.-butyl-phenyl)-N'-sec.-butyl-thiourea of melting point 103°–105° C., N-(2,4-dimethyl-6-ethyl-phenyl)-N'-tert.-butyl-thiourea of melting point 130°–132° C., N-(2,4-dimethyl-6-ethyl-phenyl)-N'-tert.-pentyl-thiourea of melting point 105°–107° C., N-(4-methyl-2,6-diethyl-phenyl)-N'-tert.-butyl-thiourea of melting point 121°–123° C., N-(4-methyl-2,6-diethyl-phenyl)-N'-tert.-pentyl-thiourea of melting point 98°–101° C., N-(2-methyl-6-ethyl-phenyl)-N'-tert.-butyl-thiourea of melting point 94°–96° C., N-(2-methyl-6-ethyl-phenyl)-N'-tert.-pentyl-thiourea of melting point 78°–81° C., N-(2,6-diethyl-3-methyl-phenyl)-N'-tert.-butyl-thiourea, N-(2,6-diethyl-3,5-dimethyl-phenyl)-N'-tert.-butyl-thiourea, N-(2,6-diethyl-3,5-dimethyl-phenyl)-N'-pent-2-yl-thiourea, N-(2,6-di-isopropyl-phenyl)-N'-(3-methyl-but-2-yl)-thiourea, N-(2,6-di-sec.-butyl-phenyl)-N'-(pent-2-yl)-thiourea, N-(2,6-di-sec.-butyl-phenyl)-N'-(hex-2-yl)-thiourea, N-(2,6-di-sec.-butyl-phenyl)-N'-(pent-3-yl)-thiourea, N-(2,6-di-sec.-butyl-phenyl)-N'-(4-methyl-pent-2-yl)-thiourea, N-(2,6-di-sec.-butyl-phenyl)-N'-(2-methyl-pent-3-yl)-thiourea, N-(2,6-diisopropyl-phenyl)-N'-(pent-2-yl)-thiourea, N-(2,6-diisopropyl-phenyl)-N'-(hex-2-yl)-thiourea, N-(2,6-diisopropyl-phenyl)-N'-(3-methyl-pent-2-yl)-thiourea, N-(2,6-diisopropyl-phenyl)-N'-(pent-3-yl)-thiourea, N-(2,6-diisopropyl-phenyl)-N'-(2,2-dimethyl-pent-3-yl)-thiourea, N-(2-ethyl-6-sec.-butyl-phenyl)-N'-tert.-butyl-thiourea of melting point 96°–99° C., N-(2-isopropyl-6-sec.-butyl-phenyl)-N'-tert.-butyl-thiourea of melting point 121°–123° C., N-(2-isopropyl-6-sec.-butyl-phenyl)-N'-tert.-butyl-thiourea of melting point 51°–53° C., N-(2,6-diisopropyl-phenyl)-N'-(1-cyclopentyl-ethyl)-thiourea, N-(2,6-di-sec.-butyl-phenyl)-N'-(2-methyl-pent-2-yl)-thiourea, N-(2,6-di-sec.-butyl-phenyl)-N'-(2-ethyl-pent-2-yl)-thiourea, N-(2,6-di-sec.-butyl-phenyl)-N'-(2-methyl-hex-2-yl)-thiourea, N-(2,6-diethyl-phenyl)-N'-(2-methyl-oct-2-yl)-thiourea, N-(2,6-diisopropyl-phenyl)-N'-(2-methyl-pent-2-yl)-thiourea, N-(2,6-diisopropyl-phenyl)-N'-(2-ethyl-pent-2-yl)-thiourea, N-(2,6-diethyl-3-chloro-phenyl)-N'-tert.-butyl-thiourea, N-(2-ethyl-6-sec.-butyl-phenyl)-N'-tert.-pentyl-thiourea of melting point 74°–76° C., N-(2,6dicyclopentyl-phenyl)-N'-tert.-butyl-thiourea, N-(2-ethyl-4-methyl-6-sec.-butyl-phenyl)-N'-tert.-butyl-thiourea, N-(2,4-dimethyl-6-tert.-butyl-phenyl)-N'-tert.-pentyl-thiourea, N-(2,6-di-pent-2-yl-phenyl)-N'-tert.-butyl-thiourea, N-(2,4-dimethyl-6-cyclohexyl-phenyl)-N'-tert.-butyl-thiourea, N-(2,6-diisopropyl-4-chlorophenyl)-N'-tert.-butyl-thiourea, N-(2,5-dimethyl-6-ethyl-phenyl)-N'-tert.-pentyl-thiourea, N-(2,5-dimethyl-6-isopropyl-phenyl)-N'-tert.-pentyl-thiourea, N-(2,6-diethyl-phenyl)-N'-(2-methyl-pent-2-yl)-thiourea, N-(2,6-diethyl-phenyl)-N'-(2-ethyl-pent-2-yl)-thiourea, N-(2,6-diethyl-phenyl)-N'-(2-methyl-hex-2-yl)-thiourea, N-(2,6-diethyl-phenyl)-N'-(dec-5-yl)-thiourea, N-(2,6-diethyl-phenyl)-N'-(1,1,2,2-tetramethyl-propyl)-thiourea, N-(2,6-diethyl-phenyl)-N'-(2,4-dimethyl-pent-3-yl)-thiourea and N-(2,6-dimethyl-phenyl)-N'-(2,2-dimethyl-pent-3-yl)-thiourea.

The compounds in the following list (List B) may be mentioned as new N-aryl-N'-cycloalkyl-thioureas of the general formula (I):

List B

N-(2-methyl-6-ethyl-phenyl)-N'-cyclopropyl-thiourea, N-(2-methyl-6-ethyl-phenyl)-N'-cyclopentyl-thiourea, N-(2-methyl-6-ethyl-phenyl)-N'-cyclohexyl-thiourea, N-(2-methyl-6-ethyl-phenyl)-N'-cycloheptyl-thiourea, N-(2,4-dimethyl-6-ethyl-phenyl)-N'-(3-methyl-cyclohexyl)-thiourea, N-(2,6-diethyl-phenyl)-N'-cyclopropyl-thiourea of melting point 111°–113° C., N-(2,6-diethyl-phenyl)-N'-cyclobutyl-thiourea, N-(2,6-diethyl-phenyl)-N'-cyclopentyl-thiourea, N-(2,6-diethyl-phenyl)-N'-(1-methyl-cyclopentyl)-thiourea of melting point 86°–88° C., N-(2,6-diethyl-phenyl)-N'-cyclohexyl-thiourea, N-(2,6-diethyl-phenyl)-N'-(2-methyl-cyclohexyl)-thiourea (oil), N-(2,6-diethyl-phenyl)-N'-cycloheptyl-thiourea, N-(2,6-diethyl-phenyl)-N'-cyclooctyl-thiourea, N-(4-methyl-2,6-diethyl-phenyl)-N'-cyclopropyl-thiourea of melting point 113°–115° C., N-(4-methyl-2,6-diethyl-phenyl)-N'-cyclopentyl-thiourea, N-(4-methyl-2,6-diethyl-phenyl)-N'-cyclohexyl-thiourea, N-(4-methyl-2,6-diethyl-phenyl)-N'-(4-methyl-cyclohexyl)-thiourea, N-(4-methyl-2,6-diethyl-phenyl)-N'-(3,3,5-trimethyl-cyclohexyl)-thiourea, N-(4-methyl-2,6-diethyl-phenyl)-N'-(2,6-diethyl-cyclohexyl)-thiourea, N-(2,4,6-triethyl-phenyl)-N'-cyclopropyl-thiourea, N-(2,4,6-triethyl-phenyl)-N'-cyclopentyl-thiourea, N-(2,4,6-triethyl-phenyl)-N'-cyclohexyl-thiourea of melting point 97°–99° C., N-(2,4,6-triethyl-phenyl)-N'-(3-trifluoromethyl-cyclohexyl)-thiourea of melting point 52°–55° C., N-(2,4,6-triethyl-phenyl)-N'-(trifluoromethyl-cyclohexyl)-thiourea, N-(2,4,6-triethyl-phenyl)-N'-(3,5-bis-trifluoromethyl-cyclohexyl)-thiourea, N-(2,4,6-triethyl-phenyl)-N'-cyclopentyl-thiourea, N-(2,4,6-triethyl-phenyl)-N'-cyclooctyl-thiourea, N-(2,4,6-triethyl-phenyl)-N'-(2-norbornyl)-thiourea, N-(2,4,6-triethyl-phenyl)-N'-(1-adamantyl)-thiourea, N-(4-n-propyl-2,6-diethyl-phenyl)-N'-cyclopentyl-thiourea, N-(4-n-propyl-2,6-diethyl-phenyl)-N'-cyclohexyl-thiourea, N-(4-n-propyl-2,6-diethyl-phenyl)-N'-(3-methyl-cyclohexyl)-thiourea, N-(4-n-propyl-2,6-diethyl-phenyl)-N'-(4-methylcyclohexyl)-thiourea, N-(4-n-propyl-2,6-diethyl-phenyl)-N'-(3-trifluoromethyl-cyclohexyl)-thiourea (oil), N-(4-n-propyl-2,6-diethyl-phenyl)-N'-(4-trifluoromethyl-cyclohexyl)-thiourea (oil), N-(4-n-propyl-2,6-diethyl-phenyl)-N'-(2,4-dimethyl-cyclohexyl)-thiourea, N-(4-n-propyl-2,6-diethyl-phenyl)-N'-(4-ethyl-cyclohexyl)-thiourea, N-(4-n-propyl-2,6-diethyl-phenyl)-N'-cyclopentyl-thiourea, N-(4-isopropyl-2,6-diethyl-phenyl)-N'-cyclopentyl-thiourea, N-(4-isopropyl-2,6-diethyl-phenyl)-N'-cyclohexyl-thiourea of melting point 120°–123° C., N-(4-isopropyl-2,6-diethyl-phenyl)-N'-(3-trifluoromethyl-cyclohexyl)-thiourea of melting point 127°–140° C., N-(4-isopropyl-2,6-diethyl-phenyl)-N'-(2-norbornyl)-thiourea, N-(4-isopropyl-2,6-diethyl-phenyl)-N'-(decahydronaphthyl-1)-thiourea, N-(4-n-butyl-2,6-diethyl-phenyl)-N'-cyclopentyl-thiourea, N-(4-n-butyl-2,6-diethyl-phenyl)-N'-cyclohexyl-thiourea (oil), N-(4-n-butyl-2,6-diethyl-phenyl)-N'-(3-methyl-cyclohexyl)-thiourea (oil), N-(4-n-butyl-2,6-diethyl-phenyl)-N'-(4-methyl-cyclohexyl)-thiourea, N-(4-n-butyl-2,6-diethyl-phenyl)-N'-(4-ethylcyclo-hexyl)-thiourea, N-(4-n-butyl-2,6-diethyl-phenyl)-N'-(3-trifluoromethyl-cyclohexyl)-thiourea (oil), N-(4-n-butyl-2,6-diethyl-phenyl)-N'-cycloheptyl-thiourea, N-(4-n-pentyl-2,6-diethylphenyl)-N'-cyclopentyl-thiourea, N-(4-n-pentyl-2,6-diethyl-phenyl)-N'-cyclohexyl-thiourea, N-(4-n-pentyl-2,6-diethyl-phenyl)-N'-cycloheptyl-thiourea, N-(4-pent-3-yl-2,6-diethyl-phenyl)-N'-cyclopentyl-thiourea, N-(4-pent-3-yl-2,6-diethyl-phenyl)-N'-cyclohexyl-thiourea, N-(4-pent-3-yl-2,6-diethyl-phenyl)-N'-(3-trifluoromethylcyclohexyl)-thiourea, N-(4-pent-3-yl-2,6-diethyl-phenyl)-N'-cycloheptyl-thiourea, N-(4-n-hexyl-2,6-diethyl-phenyl)-N'-cyclopentyl-thiourea, N-(4-n-hexyl-2,6-diethyl-phenyl)-N'-cyclohexyl-thiourea, N-(4-cyclohexyl-2,6-diethyl-phenyl)-N'-cyclopentyl-thiourea, N-(4-cyclohexyl-2,6-diethyl-phenyl)-N'-cyclopropyl-thiourea, N-(4-cyclohexyl-2,6-diethyl-phenyl)-N'-(3-trifluoromethyl-cyclohexyl)-thiourea of melting point 118°–125° C., N-(4-(1-methyl-cyclohexyl)-2,6-diethyl)-N'-cyclopentyl-thiourea, N-(4-cyclo-pentyl-2,6-diethyl-phenyl)-N'-cyclopentyl-thiourea, N-(4-cyclopentyl-2,6-diethyl-phenyl)-N'-cyclohexyl-thiourea, N-(4-cyclopentyl-2,6-diethyl-phenyl)-N'-(cyclohex-2-enyl)-thiourea, N-(4-sec.-butyl-2,6-diethyl-phenyl)-N'-cyclopentyl-thiourea, N-(4-sec.-butyl-2,6-diethyl-phenyl)-N'-cyclohexyl-thiourea of melting point 140° C., N-(4-sec.-butyl-2,6-diethyl-phenyl)-N'-(2-methyl-cyclohexyl)-thiourea (oil), N-(4-sec.-butyl-2,6-diethyl-phenyl)-N'-(3-methyl-cyclohexyl)-thiourea (oil), N-(4-sec.-butyl-2,6-diethyl-phenyl)-N'-(4-methyl-cyclohexyl)-thiourea of melting point 86°–123° C., N-(4-sec.-butyl-2,6-diethyl-phenyl)-N'-(3-trifluoromethyl-cyclohexyl)-thiourea, N-(4-sec.-butyl-2,6-diethyl-phenyl)-N'-cycloheptyl-thiourea, N-(4-sec.-butyl-2,6-diethyl-phenyl)-N'-(3,3,5-trimethyl-cyclohexyl)-thiourea of melting point 58°–80° C., N-(4-isobutyl-2,6-diethyl-phenyl)-N'-cyclopropyl-thiourea, N-(4-isobutyl-2,6-diethyl-phenyl)-N'-cyclobutyl-thiourea, N-(4-isobutyl-2,6-diethyl-phenyl)-N'-cyclopentyl-thiourea, (oil), N-(4-isobutyl-2,6-diethyl-phenyl)-N'-cyclohexyl-thiourea of melting point 41°–44° C., N-(4-isobutyl-2,6-diethyl-phenyl)-N'-(1-methyl-cyclopentyl)-thiourea of melting point 73°–74° C., N-(4-isobutyl-2,6-diethyl-phenyl)-N'-(2-methyl-cyclohexyl)-thiourea (resin), N-(4-isobutyl-2,6-diethyl-phenyl)-N'-(3-methyl-cyclohexyl)-thiourea of melting point 57°–85° C., N-(4-isobutyl-2,6-diethyl-phenyl)-N'-(4-methyl-cyclohexyl)-thiourea of melting point 70°–105° C., N-(4-isobutyl-2,6-diethyl-phenyl)-N'-(3-trifluoromethyl-cyclohexyl-thiourea of melting point 50°–55° C., N-(4-isobutyl-2,6-diethyl-phenyl)-N'-(4-trifluoromethyl-cyclohexyl)-thiourea of melting point 52°–60° C., N-(4-isobutyl-2,6-diethyl-phenyl)-N'-(2,6-dimethylcyclohexyl-thiourea, N-(4-isobutyl-2,6-diethyl-phenyl)-N'-(2-norbornyl)-thiourea, N-(4-isobutyl-2,6-diethyl-phenyl)-N'-(1-adamantyl)-thiourea, N-(4-isobutyl-2,6-diethyl-phenyl)-N'-cycloheptyl-thiourea, N-(4-cycloheptyl-2,6-diethyl-phenyl-N'-cyclopentyl-thiourea, N-(2,6-diisopropyl-phenyl)-N'-cyclopropylthiourea of melting point 166°–168° C., N-(2,6-diisopropyl-phenyl)-N'-cyclopentyl-thiourea of melting point 140°–142° C., N-(2,6-diisopropyl-phenyl)-N'-(1-methyl-cyclopentyl)-thiourea of melting point 149°–150° C., N-(2,6-diisopropyl-phenyl)-N'-cyclohexyl-thiourea of melting point 120°–122° C., N-(2,6-diisopropyl-phenyl)-N'-(2-methyl-cyclohexyl)-thiourea of melting point 128°–145° C., N-(2,6-diisopropyl-phenyl)-N'-(3-methyl-cyclohexyl)-thiourea of melting point 62°–76° C., N-(2,6-diisopropyl-phenyl)-N'-(4-methyl-cyclohexyl)-thiourea of melting point 155°–167° C., N-(2,6-diisopropyl-phenyl)-N'-(2-trifluoro-methyl-cyclohexyl)-thiourea of melting point 187° C., N-(2,6-diisopropyl-phenyl)-N'-(3-trifluoromethylcyclohexyl)-thiourea of m.p. 67°–75° C., N-(2,6-diisopropyl-phenyl)-N'-(4-trifluoromethyl-cyclohexyl)-thiourea of melting point 142°–165° C., N-(2,4,6-triisopropyl-phenyl)-N'-cyclopropyl-thiourea of melting point 158°–160° C., N-(2,6-diisopropyl-phenyl)-N'-(4-ethyl-cyclohexyl)-thiourea, N-(2,6-diisopropyl-phenyl)-N'-(cyclohex-2-enyl)-thiourea, N-(2,6-diisopropyl-phenyl)-N'-(3,3,5-trimethyl-cyclohexyl)-thiourea of melting point 84°–120° C., N-(2,6-diisopropyl-phenyl)-N'-(3,5-bis-trifluoromethyl-cyclohexyl)-thiourea of melting point 180°–182° C., N-(2,6-diisopropyl-phenyl)-N'-(2,4-dimethylcyclohexyl)-thiourea, N-(2,6-diisopropyl-phenyl)-N'-(3-trifluoromethyl-4-methyl-cyclohexyl)-thiourea of melting point 145°–165° C., N-(2,6-diisopropyl-phenyl)-N'-(2-norbornyl)-thiourea, N-(2,6-diisopropyl-phenyl)-N'-(1-adamantyl)-thiourea, N-(2,6-diisopropyl-phenyl)-N'-cycloheptyl-thiourea, N-(2-ethyl-6-isopropyl-phenyl)-N'-cyclohexyl-thiourea, N-(4-methyl-2,6-diisopropyl-phenyl)-N'-cyclopentyl-thiourea, N-(2-isopropyl-6-sec.-butyl-phenyl)-N'-cyclopentyl-thiourea, N-(2,6-di-sec.-butyl-phenyl)-N'-cyclopropyl-thiourea of melting point 151°–153° C., N-(2,6-di-sec.-butyl-phenyl)-N'-cyclopentyl-thiourea of melting point 140°–142° C., N-(2,6-di-sec.-butyl-phenyl)-N'-(1-methyl-cyclopentyl)-thiourea, N-(2,6-di-sec.-butyl-phenyl)-N'-cyclohexylthiourea, N-(2,6-di-sec.-butyl-phenyl)-N'-(3-methylcyclohexyl)-thiourea, N-(2,6-di-sec.-butyl-phenyl)-N'-(3-trifluoromethyl-cyclohexyl)-thiourea of melting point 58°–67° C., N-(2,6-di-sec.-butyl-phenyl)-N'-(3,5-bis-trifluoromethyl-cyclohexyl)-thiourea (oil), N-(2,6-di-sec.-butyl-phenyl)-N'-(2-norbornyl)-thiourea, N-(2,6-di-sec.-butyl-phenyl)-N'-cycloheptyl-thiourea, N-(2-ethyl-6-sec.-butyl-phenyl)-N'-cyclopropyl-thiourea of melting point 122°–123° C., N-(2,6-di-cyclopentyl-phenyl)-N'-cyclopentyl-thiourea of melting point 168°–170° C., N-(2,6-di-cyclopentyl-phenyl)-N'-cyclohexyl-thiourea, N-(di-pent-2-yl-phenyl)-N'-cyclopentyl-thiourea, N-(di-pent-2-yl-phenyl)-N'-cyclohexyl-thiourea, N-(2-chloro-2,6-diethyl-phenyl)-N'-cyclopropyl-thiourea of melting point 130°–131° C., N-(3-methyl-2,6-diethyl-phenyl)-N'-cyclopropyl-thiourea of melting point 145°–146° C., N-(3,5-dimethyl-2,6-diethyl-phenyl)-N'-cyclopropyl-thiourea of melting point 145°–146° C., N-(4-methyl-2,6-di-sec.-butyl-phenyl)-N'-cyclopropyl-thiourea of melting point 154°–156° C., N-(2,4,6-diethyl-phenyl)-N'-cycloheptyl-thiourea of melting point 84°–86° C., N-(4-n-propyl-2,6-diethyl-phenyl)-N'-cycloheptyl-thiourea (oil), N-(4-isopropyl-2,6-diethyl-phenyl)-N'-cycloheptyl-thiourea of melting point 89°–92° C. and N-(4-n-butyl-2,6-diethyl-phenyl)-N'-cycloheptyl-thiourea (oil).

The active compounds are well tolerated by plants, have a favourable level of toxicity to warm-blooded animals, and can be used for combating animal pests, especially insects arachnidae and nematodes which are encountered in veterinary medicine, agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus Differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocollecties blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euoxa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example Diprion spp., Hoplocampa spp., Lasium spp., *Monomorium pharaonis* and Vespa spp. From the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The compounds according to the invention are also active against harmful fungi, especially Pyricularia and Pellicularia.

The active compounds according to the invention are used in the form of their commercially available formulations and/or in the use forms prepared from these formulations.

The active compound content of the use forms prepared from the commercially available formulations can vary within wide ranges. The active compound concentration of the use forms can be from 0.0000001 to 100% by weight of active compound, preferably between 0.01 and 10% by weight.

The compounds are employed in a customary manner appropriate for the particular use forms.

The active compounds according to the invention can be used in the veterinary field in a known manner, such as by oral application alone in admixture with a diluent or in the form of, for example tablets, capsules, drinks and granules, by dermal application for example by dipping (dips), spraying (sprays), pouring-on (pour on and spot on) and powdering, as well as by parenteral application in the form of, for example injection.

The present invention therefore provides a pesticidal composition containing as active ingredient a compound of the invention in admixture with a solid or liquefied gaseous diluent, or in admixture with a liquid diluent other than a solvent of a molecular weight less than 200 (preferably less than 350) except in the presence of a surface-active agent.

The invention further provides a pesticidal composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pesticidal compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and mangesium stearate and solid polyethylene glycols.

The tablets, dragees, capsules and pills formed from the compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in compositions adapted to be formed into suppositories, can for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the compositions according to the invention can also contain colouring agents and preservatives as well as perfumes and flavouring additions (e.g. peppermint oil and eucalyptus oil) and sweetening agents (e.g. saccharin).

The compositions according to the invention generally contain from 0.1 to 99.5 m usually from 0.5 to 95% of the active ingredient by weight of the total composition.

In addition to a compound of the invention, the compositions and medicaments according to the invention can also contain other parasitically active compounds. They may also contain a plurality of compounds of the invention.

Any diluent in the medicaments of the present invention may be any of those mentioned above in relation to the pesticidal compositions of the present invention. Such medicaments may include solvents of molecular weight less than 200 as sole diluent.

The discrete coherent portions constituting the medicament according to the invention will generally be adapted by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pesticidal compositions and medicaments is carried out by any method known in the art, for example, by mixing the active ingredient(s) with the diluent(s) to form a composition (e.g. a granulate) and then forming the composition into the medicament (e.g. tablets).

The invention further provides a method of combating animal and plant pests which comprises applying to the pest, or to a habitat thereof, a compound of the invention alone or in admixture with a diluent or carrier.

The invention specifically includes a method of freeing or protecting domesticated animals from ectoparasites which comprises applying or administering to the animals a compound of the invention alone or in admixture with a diluent or in the form of a medicament. The treatment rates used will vary as a function of the nature and body weight of the human or animal subject to be treated, the individual reaction of this subject to be treated, the individual reaction of this subject to the treatment, the type of formulation in which the active ingredient is administered and the mode in which the administration is carried out, and the point in the progress of the infection or interval at which it is to be administered. Where large amounts are administered it can be advisable to divide these into several individual administrations over the course of the day.

The active compounds can also be converted to the customary formulations used in plant protection, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers: ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules: crushed and fractionated natural rocks such as calcite, marble, pumice, sepiolite and dolomite, as well as synthetic granules or inorganic and organic meals, and granules of organic material such as sawdust, coconut shells, maize cobs and tobacco stalks; as emulsifying and/or foam-forming agents: non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents: for example lignin, sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azometal phthalocyanine dyestuffs, and trace nutrients such as salts of iron, maganese, boron, copper, cobalt, molybdenum and zinc.

The formulations in general contain between 0.1 and 95 percent by weight of active compound, preferably between 0.5 and 90%.

The following Examples A to D illustrate the pesticidal activity of the compounds of the invention.

Example A

In vivo tick test on *Boophilus microplus*

3 parts by weight of the active compound listed in Table A are mixed with 7 parts of a mixture of equal parts by weight of ethylene glycol monomethyl ether and nonylphenyl polyglycol ether. The emulsion concentrate thus obtained is diluted with water to the particular desired use concentration.

Cattle which have been infected repeatedly (12 infections at intervals of 2 days) with resistant tick larvae of the species *Boophilus microplus*, Biarra strain, are sprayed with the active compound preparation thus obtained.

The action of the active compound preparation is measured by determining the number of the adult female ticks which develop on the treated cattle. This number is compared with the number of adult female ticks which develop on untreated cattle. A compound is the more active, the fewer female ticks develop after the treatment.

The number of adult females which, in treated and untreated animals, develop in the last three days before the time of treatment, is used as a measure of the severity of the infection before the treatment. The results are set out in Table A.

TABLE A1

| Ex- ample No. | Active compound concentration and active compound | days before treatment −2-±0 | in vivo — Number of ticks with fertile eggs — days after treatment | | | | | | Σ +1-21 | Action in % |
|---|---|---|---|---|---|---|---|---|---|---|
| | | | +1-3 | 4-6 | 7-9 | 10-12 | 13-15 | 16-18 | 19-21 | | |
| (comparative) | Known from DT-OS (German Published Specification) 2,337,122: 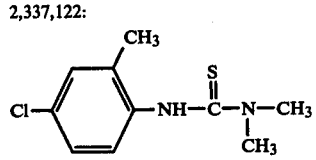 1.000 ppm according to the invention | 1910 | 132 | 37 | 35 | 54 | 15 | 0 | 0 | 273 | 97,63 |

TABLE A1-continued

| Example No. | Active compound concentration and active compound | in vivo days before treatment −2−±0 | Number of ticks with fertile eggs days after treatment | | | | | | | Σ +1-21 | Action in % |
|---|---|---|---|---|---|---|---|---|---|---|---|
| | | | +1-3 | 4-6 | 7-9 | 10-12 | 13-15 | 16-18 | 19-21 | | |
| A1 | CH₃—CH₂CH(CH₃)—[2,6-di-sec-butylphenyl]—NH—C(S)—NH—C(CH₃)₃ 250 ppm | 1244 | 21 | 12 | 10 | 10 | 2 | 0 | 0 | 55 | 98,5 |
| A2 | [2,6-diethylphenyl]—NH—C(S)—NH—C(CH₃)₃ 250 ppm | 595 | 21 | 0 | 27 | 8 | 0 | 0 | 0 | 56 | 96,5 |

Tick test

Solvent:
35 parts by weight of ethylene glycol monomethyl ether
35 parts by weight of nonylphenol polyglycol ether To prepare a suitable formulation, three parts by weight of the active compound ot Table A2 are mixed with seven parts of the abovementioned solvent/emulsifier mixture and the emulsion concentrate thus obtained in diluted with water to the particular concentration desired.

Adult, fully bloated female ticks of the species Boophilus microplus (sensitive or resistant) are dipped for one minute into these active compound preparations. After dipping 10 female specimens of each of the various species of ticks, the specimens are transferred into Petri dishes, the bottom of which is lined with a filter disc of corresponding size.

After 10 days, the activity of the active compound preparation is determined by examining the inhibition of the laying of eggs, as compared to untreated control ticks. This action is expressed as a percentage, with 100% denoting that eggs were no longer laid and 0% denoting that the ticks laid normal numbers of eggs.

The active compound examined, the concentration tested, the parasites tested and the findings obtained can be seen from the Table which follows.

TABLE A2

| Example No. | Active compound according to the invention | Active compound concentration in ppm | Destructive action in % Boophilus microplus res. |
|---|---|---|---|
| A2 | 2,6-di-isopropylphenyl—NH—C(S)—NH—C(CH₃)₃ | 10.000 | 100 |
| | | 1.000 | >50 |
| A3 | 2,6-di-isopropylphenyl—NH—C(S)—NH—C(CH₃)(C₂H₅)(CH₃) | 10.000 | 100 |
| | | 1.000 | 100 |

TABLE A2-continued

| Example No. | Active compound according to the invention | Active compound concentration in ppm | Destructive action in % Boophilus microplus res. |
|---|---|---|---|
| A4 | 2,6-diethylphenyl-NH-C(=S)-NH-C(CH₃)₃ | 10.000<br>1.000 | 100<br>>50 |
| A5 | 2,6-diethylphenyl-NH-C(=S)-NH-C(CH₃)₂C₂H₅ | 10.000<br>1.000 | 100<br>>50 |
| A6 | 2,6-bis(sec-butyl)phenyl-NH-C(=S)-NH-C(CH₃)₂C₂H₅ | 10.000<br>1.000 | 100<br>>50 |
| A7 | 2,6-bis(sec-butyl)phenyl-NH-C(=S)-NH-C(CH₃)₃ | 10.000<br>1.000<br>100 | 100<br>100<br><50 |
| A8 | 2,6-diethylphenyl-NH-C(=S)-NH-CH(CH₃)(C₂H₅) | 10.000<br>1.000 | 100<br><50 |
| A9 | 4-methyl-2,6-diethylphenyl-NH-C(=S)-NH-C(CH₃)₃ | 10.000<br>1.000 | 100<br>>50 |
| A10 | 4-methyl-2,6-diethylphenyl-NH-C(=S)-NH-C(CH₃)₂C₂H₅ | 10.000<br>1.000 | 100<br>>50 |
| For comparison: | 4-chloro-2-methylphenyl-NH-C(=S)-N(CH₃)₂ | 1.000<br>100 | <50<br>0 |

Example B

Test with parasitic fly larvae

Solvent: 35 parts by weight of ethylene polyglycol monomethyl ether
35 parts by weight of nonylphenol polyglycol ether To produce a suitable preparation of active compound, 30 parts by weight of the active substance indicated in Table B are mixed with the stated amount of solvent, which contains the abovementioned proportion of emulsifier and the concentrate thus obtained is diluted with water to the desired concentration.

About 20 fly larvae (*Lucilia cuprina*) are introduced into a test tube which contains approx. 2 cm³ of horse muscle. 0.5 ml of the preparation of active compound is applied to this horse meat. After 24 hours, the degree of destruction in % is determined. 100% means that all larvae have been killed and 0% means that no larvae have been killed.

| Example No. | Active compound | Active compound concentration in ppm | Destructive action in % Lucilia cuprina res. |
|---|---|---|---|
| B1 | 2,6-bis(isopropyl)phenyl-NH-C(=S)-NH-C(CH₃)₃ | 1.000<br>300 | 100<br>100 |
| B2 | 2,6-bis(sec-butyl)phenyl-NH-C(=S)-NH-C(CH₃)₂C₂H₅ | 1.000 | 100 |
| B3 | 2,6-bis(sec-butyl)phenyl-NH-C(=S)-NH-C(CH₃)₃ | 1.000<br>300<br>100 | 100<br>100<br>>50 |
| B4 | 2,6-diethyl-4-methylphenyl-NH-C(=S)-NH-C(CH₃)₃ | 1.000 | 100 |

TABLE B

| Example No. | Active compound | Active compound concentration in ppm | Destructive action in % Psoroptes cuniculi |
|---|---|---|---|
| B5 | 2,6-bis(isopropyl)phenyl-NH-C(=S)-NH-C(CH₃)₃ | 1.000<br>300<br>100 | 100<br>100<br>100 |

TABLE B-continued
| Example No. | Active compound | Active compound concentration in ppm | Destructive action in % Psoroptes cuniculi |
|---|---|---|---|
| B6 | 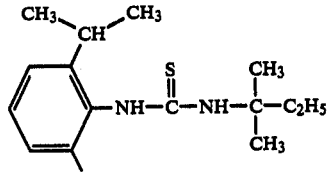 | 1.000<br>100 | 100<br>100 |
| B7 | 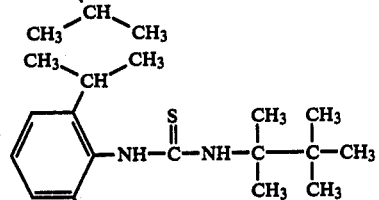 | 1.000<br>100<br>10 | 100<br>100<br>100 |
| B8 | 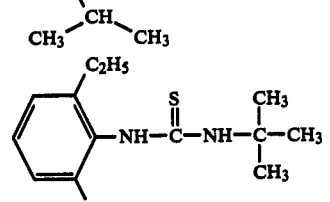 | 1.000<br>100<br>10<br>1 | 100<br>100<br>100<br>100 |
| B9 | 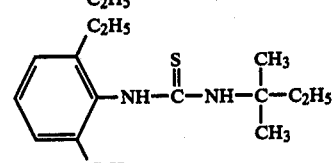 | 1.000<br>100<br>10<br>1 | 100<br>100<br>100<br>>50 |
| B10 | 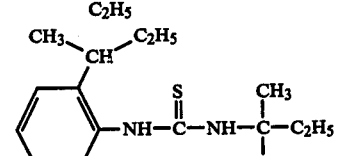 | 1.000<br>100<br>10<br>1 | 100<br>100<br>100<br>100 |
| B11 | 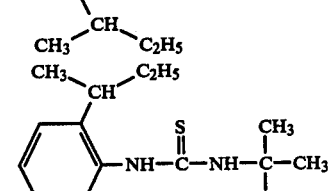 | 1.000<br>100<br>10<br>1 | 100<br>100<br>100<br>50 |
| B12 | 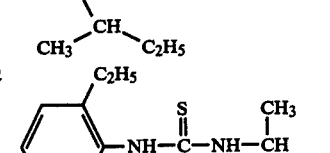 | 1.000<br>100 | 100<br>100 |
| B13 | 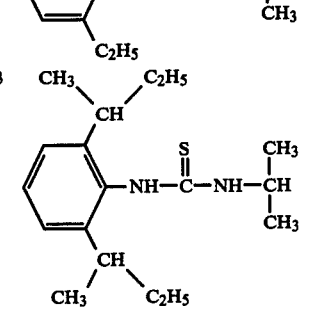 | 1.000<br>100<br>10 | 100<br>100<br>100 |

TABLE B-continued

| Example No. | Active compound | Active compound concentration in ppm | Destructive action in % Psoroptes cuniculi |
|---|---|---|---|
| B14 | 2,6-bis(1-methylpropyl)phenyl — NH—C(=S)—NH—CH(CH$_3$)(CH$_2$C$_2$H$_5$) (structure shown) | 1.000<br>100<br>10 | 100<br>100<br>100 |
| B15 | 2-methyl-6-ethylphenyl — NH—C(=S)—NH—C(CH$_3$)$_3$ | 1.000<br>100 | 100 |
| B16 | 2-methyl-6-propylphenyl — NH—C(=S)—NH—C(CH$_3$)$_2$(C$_2$H$_5$) | 1.000<br>100 | 100<br>100 |
| B17 | 2-methyl-4-methyl-6-ethylphenyl — NH—C(=S)—NH—C(CH$_3$)$_3$ | 1.000<br>100 | 100<br>100 |
| B18 | 2-ethyl-4-methyl-6-ethylphenyl — NH—C(=S)—NH—C(CH$_3$)$_3$ | 1.000<br>100 | 100<br>100 |
| B19 | 2-ethyl-4-methyl-6-ethylphenyl — NH—C(=S)—NH—C(CH$_3$)$_2$(C$_2$H$_5$) | 1.000 | 100 |
| B20 | 2-methyl-4-methyl-6-ethylphenyl — NH—C(=S)—NH—C(CH$_3$)$_2$(C$_2$H$_5$) | 1.000 | 100 |

Example C

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound indicated in Table C is mixed with the stated amount of solvent and the stated amount of emulsifier and the concentrate is diluted with water to the desired concentration.

Bean plants (*Phaseolus vulgaris*) which are heavily infested with the common or two-spotted spider mite (*Tetranychus urticae*) in all stages of development are sprayed with the preparation of the active compound until dripping wet.

After the specified periods of time, the degree of destruction is determined as a percentage: 100% means that all the spider mites are killed whereas 0% means that none of the spider mites are killed.

The active compounds, the concentrations of the active compounds, the evaluation times and the results can be seen from the following Table:

Table C (mites which damage plants)

Tetranychus test (resistant)

| Example No. | Active compounds | Active compound concentration in % | Degree of destruction in % after 2 days |
|---|---|---|---|
| Comparative | 4-Cl-2-CH$_3$-C$_6$H$_3$-NH-CS-N(CH$_3$)$_2$ (known) | 0,1<br>0,01 | 60<br>0 | active compounds according to the invention

| Example No. | Active compounds | Active compound concentration in % | Degree of destruction in % after 2 days |
|---|---|---|---|
| C1 | 2,6-bis(1-methylpropyl)phenyl-NH-CS-NH-CH(CH$_3$)$_2$ | 0,1<br>0,01 | 100<br>100 |
| C2 | 2,6-bis(1-methylpropyl)phenyl-NH-CS-NH-CH(CH$_3$)(C$_2$H$_5$) | 0,1<br>0,01 | 100<br>100 |
| C3 | 2-(1-methylpropyl)-6-(1-methylbutyl)phenyl-NH-CS-NH-C(CH$_3$)$_3$ | 0,1<br>0,01 | 100<br>100 |
| C4 | 2,6-bis(1-methylpropyl)phenyl-NH-CS-NH-C(CH$_3$)$_3$ | 0,1<br>0,01 | 100<br>70 |
| C5 | 2-ethyl-4-methyl-6-ethylphenyl-NH-CS-NH-C(CH$_3$)$_2$(C$_2$H$_5$) | 0,1<br>0,01 | 100<br>99 |

Table C-continued (mites which damage plants)
Tetranychus test (resistant)

| Example No. | Active compounds | Active compound concentration in % | Degree of destruction in % after 2 days |
|---|---|---|---|
| C6 | 2,6-bis(isopropyl)phenyl-NH-CS-NH-C(CH$_3$)(CH$_3$)(C$_2$H$_5$) | 0,1<br>0,01 | 100<br>99 |
| C7 | 2-C$_2$H$_5$,6-C$_2$H$_5$-phenyl-NH-C(S)-NH-(2-CH$_3$-cyclohexyl) | 0,1<br>0,01 | 100<br>100 |
| C8 | 2,6-(C$_2$H$_5$)$_2$-phenyl-NH-C(S)-NH-(2-CH$_3$-cyclohexyl) | 0,1<br>0,01 | 100<br>100 |
| C9 | 2,4,6-(C$_2$H$_5$)$_3$-phenyl-NH-C(S)-NH-cyclohexyl | 0,1<br>0,01 | 100<br>100 |
| C10 | 2,4,6-(C$_2$H$_5$)$_3$-phenyl-NH-C(S)-NH-(3-CF$_3$-cyclohexyl) | 0,1<br>0,01 | 100<br>100 |
| C11 | 2,6-(iso-C$_3$H$_7$)$_2$-phenyl-NH-C(S)-NH-CH$_2$-cyclohexyl | 0,1<br>0,01 | 100<br>100 |
| C12 | 2,6-(iso-C$_3$H$_7$)$_2$-phenyl-NH-C(S)-NH-(2-CH$_3$-cyclohexyl) | 0,1<br>0,01 | 100<br>100 |
| C13 | 2,6-(iso-C$_3$H$_7$)$_2$-phenyl-NH-C(S)-NH-(3-CH$_3$-cyclohexyl) | 0,1<br>0,01 | 100<br>100 |

Table C-continued (mites which damage plants)
Tetranychus test (resistant)

| Example No. | Active compounds | Active compound concentration in % | Degree of destruction in % after 2 days |
|---|---|---|---|
| C14 | 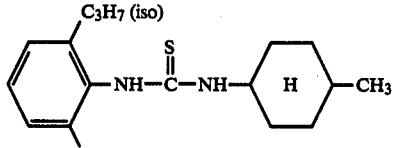 C3H7 (iso) / C3H7 (iso) aryl-NH-C(=S)-NH-cyclohexyl(H)(CH3) | 0,1<br>0,01 | 100<br>100 |
| (Comparative) | 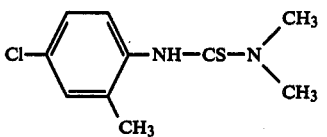 4-Cl, 2-CH3-phenyl-NH-CS-N(CH3)2 (known) | 0,1<br>0,01 | 60<br>0 |
| C15 | 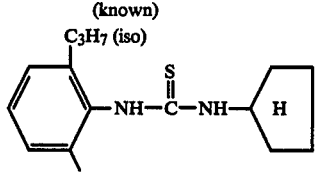 2,6-di-iso-C3H7-phenyl-NH-C(=S)-NH-cyclopentyl(H) | 0,1<br>0,01 | 100<br>99 |
| C16 | 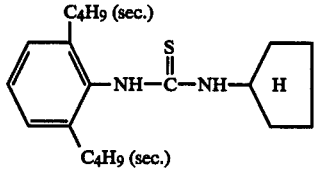 2,6-di-sec-C4H9-phenyl-NH-C(=S)-NH-cyclopentyl(H) | 0,1<br>0,01 | 100<br>100 |
| C17 | 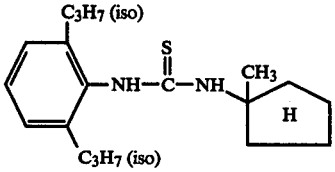 2,6-di-iso-C3H7-phenyl-NH-C(=S)-NH-(1-methylcyclopentyl) | 0,1<br>0,01 | 100<br>100 |
| C18 | 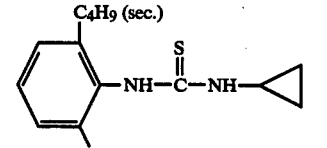 2-sec-C4H9, 6-sec-C4H9-phenyl-NH-C(=S)-NH-cyclopropyl | 0,1<br>0,01 | 100<br>100 |

Example D

Plutella test
Solvent: 3 parts by weight of dimethylformamide
Emulsifier: 1 part by weight of alkylaryl polyglycol ether To produce a suitable preparation of active compound, 1 part by weight of the active compound indicated in Table D is mixed with the stated amount of solvent containing the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation times and the results can be seen from the following Table:

Table D

(insects which damage plants)
Plutella test

| Example No. | Active compounds | Active compound concentration in % | Degree of destruction in % after 3 days |
|---|---|---|---|
| (comparative) | 4-Cl, 2-CH₃-phenyl-NH—CS—N(CH₃)₂ (known) | 0.1 | 80 |
| | active compounds according to the invention | | |
| D1 | 2,6-bis(1-methylpropyl), phenyl-NH—CS—NH—CH(CH₃)₂ (with additional 4-sec-butyl) | 0,1 / 0,01 | 100 / 100 |
| D2 | 2,6-bis(1-methylpropyl)phenyl-NH—CS—NH—CH(CH₃)₂ | 0,1 / 0,01 | 100 / 100 |
| D3 | 2,6-diethylphenyl-NH—CS—NH—C(CH₃)₃ | 0,1 / 0,01 | 100 / 95 |
| D4 | 2,6-diethyl-4-methylphenyl-NH—CS—NH—C(CH₃)₃ | 0,1 / 0,01 | 100 / 90 |
| D5 | 2,6-diisopropylphenyl-NH—CS—NH—C(CH₃)₃ | 0,1 / 0,01 | 100 / 100 |
| D6 | 2,6-bis(1-methylpropyl)phenyl-NH—CS—NH—C(CH₃)₃ | 0,1 / 0,01 | 100 / 100 |
| D7 | 2,6-diethyl-4-methylphenyl-NH—CS—NH—C(CH₃)(C₂H₅)(CH₃) | 0,1 / 0,01 | 100 / 100 |

Table D-continued (insects which damage plants)
Plutella test

| Example No. | Active compounds | Active compound concentration in % | Degree of destruction in % after 3 days |
|---|---|---|---|
| D8 | 2,6-bis(isopropyl)phenyl-NH-CS-NH-C(CH₃)(C₂H₅)(CH₃), with additional CH(CH₃)₂ at other position | 0,1<br>0,01 | 100<br>100 |
| D9 | 2,6-bis(sec-butyl... CH(CH₃)(C₂H₅))phenyl-NH-CS-NH-C(CH₃)(C₂H₅)(CH₃) | 0,1<br>0,01 | 100<br>100 |
| D10 | 2,6-bis(isopropyl)phenyl-NH-CS-NH-C(CH₃)₂-C(CH₃)₃ (comparative) | 0,1<br>0,01 | 100<br>100 |
| | 4-Cl-2-CH₃-phenyl-NH-CS-N(CH₃)₂ (known) | 0,1<br>0,01 | 80<br>0 |
| D11 | 2,6-bis(sec-C₄H₉)phenyl-NH-C(=S)-NH-cyclopentyl | 0,1<br>0,01 | 100<br>90 |
| D12 | 2,6-bis(iso-C₃H₇)phenyl-NH-C(=S)-NH-(1-methylcyclopentyl) | 0,1<br>0,01 | 100<br>95 |
| D13 | 2,4,6-tris(iso-C₃H₇)phenyl-NH-C(=S)-NH-cyclopropyl | 0,1<br>0,01 | 100<br>90 |
| D14 | 2,6-bis(sec-C₄H₉)-4-CH₃-phenyl-NH-C(=S)-NH-cyclopropyl | 0,1<br>0,01 | 100<br>90 |

Table D-continued (insects which damage plants)
Plutella test

| Example No. | Active compounds | Active compound concentration in % | Degree of destruction in % after 3 days |
|---|---|---|---|
| D15 | C4H9—[phenyl with 2,6-diethyl substituents]—NH—C(=S)—NH—[cyclohexyl, H] | 0,1<br>0,01 | 100<br>90 |

The following Examples illustrate the preparation of particular compounds of the invention.

EXAMPLE 1

N-(2,6-Di-sec.-butyl-phenyl)-N'-tert.-butyl-thiourea 20.6 g of 2,6-di-sec.-butyl-phenyl isothiocyanate are dissolved in 20.0 g of tert.-butylamine and the batch is kept for 12 hours at 20° C. It is then poured into dilute hydrochloric acid and the reaction product is filtered off, washed until neutral and dried.

Yield 25.0 g; 96% of theory. Melting point: 115°–117° C.

2,6-Di-sec.-butyl-phenyl isothiocyanate, used as the starting material, can be prepared as follows:

100 g of 2,6-di-sec.-butyl-aniline in 200 ml of methylene chloride are added dropwise at 0°–5°, whilst stirring, to a mixture of 300 ml of water, 500 ml of methylene chloride, 100 g of calcium carbonate and 68 g of thiophosgene. The mixture is then warmed under reflux until the evolution of gas has ended. After cooling the mixture, the solids are filtered off and the methylene chloride layer is separated off, dried over calcium chloride and fractionated: boiling point 117°–120° C./1.0 mm Hg; yield 112 g; 93% of theory.

EXAMPLE 2

Analogously in Example 1, 2,6-di-sec.-butyl-phenyl isothiocyanate and tert.-pentylamine give N-(2,6-di-sec.-butyl-phenyl)-N'-tert.-butyl-thiourea of melting point 116°–118° C.

EXAMPLES 3 TO 6

The following compounds are prepared analogously to Example 1:

Example 3: from 2-ethyl-6-sec.-butylphenyl isothiocyanate and tert.-butylamine, the compound N-(2-ethyl-6-sec.-butyl-phenyl)-N'-tert.-butyl-thiourea of melting point 96°–99° C.;

Example 4: from 2-ethyl-6-sec.-butyl-phenyl isothiocyanate and tert.-pentylamine, the compound N-(2-ethyl-6-sec.-butyl-phenyl)-N'-tert.-pentyl-thiourea of melting point 74°–76° C.;

Example 5: from 2-isopropyl-6-sec.-butyl-phenyl isothiocyanate and tert.-butylamine, the compound N-(2-isopropyl-6-sec.-butyl-phenyl)-N'-tert.-butyl-thiourea of melting point 121°–123° C.;

Example 6: from 2-isopropyl-6-sec.-butyl-phenyl) isothiocyanate and tert.-pentylamine, the compound N-(2-isopropyl-6-sec.-butyl-phenyl)-N'-tert.-pentyl-thiourea of melting point 51°–53° C.

EXAMPLE 7

N-(2,6-Diisopropyl-phenyl)-N'-tert.-butyl-thiourea 15 g of 2,6-diisopropyl-phenyl isothiocyanate are introduced into 25 g of tert.-butylamine and kept for 12 hours at 20° C. The mixture is then poured into dilute hydrochloric acid and the product is filtered off, washed and dried. Yield 17 g, melting point: 135°–137°.

2,6-Diisopropyl-phenyl isothiocyanate used as the starting compound can be prepared as follows: 100 g of 2,6-diisopropyl-phenyl isothiocyanate in 200 ml of methylene chloride are added dropwise at 0°–5°, whilst stirring, to a mixture of 300 ml of water, 500 ml of methylene chloride, 120 g of calcium carbonate and 78 g of thiophosgene. The mixture is then warmed under reflux until the evolution of $CO_2$ has ended. After it has cooled, the mixture is filtered and the methylene chloride layer is separated off, dried over calcium chloride and fractionated.

Yield 110 g; boiling point 144°–148° C./11 mm Hg.

EXAMPLE 8

The same compound as Example 7 can also be obtained in the following manner: 50 g of 2,6-diisopropyl-phenyl isothiocyanate and 19.0 g of tert.-butylamine in 250 ml of benzene and 20 ml of triethylamine are heated under reflux for 5 hours. The solvent is then distilled off and the residue is caused to crystallise by means of petroleum ether.

Yield 34 g, melting point: 135°–137°.

EXAMPLE 9

N-(2,6-Diisopropyl-phenyl)-N'-tert.-pentyl-thiourea 11.0 g of 2,6-diisopropyl-phenyl isothiocyanate and 10 g of tert.-pentylamine are warmed with 5 ml of triethylamine for 10 minutes at 100°. After standing for 12 hours, the mixture which has partially crystallised out is stirred with petroleum ether and cooled to −10° C., and the product is filtered off and dried.

Yield 14.0 g; melting point: 134°–135° C.

EXAMPLE 10

N-(2,6-Diisopropyl-phenyl)-N'-(1,1,2,2-tetramethyl-propyl)-thiourea, melting point: 161°–162° C., is obtained by reacting 15.0 g of 2,6-diisopropyl-phenyl isothiocyanate with 9.0 g of 1,1,2,2-tetramethyl-propylamine in 10 ml of triethylamine, as described in Example 9.

EXAMPLE 11

N-(2,6-Diethyl-phenyl)-N'-tert.-butyl-thiourea 20 g of 2,6-diethyl-phenyl isothiocyanate are introduced into 20 g of tert.-butylamine. The mixture is cooled so that 40° C. is not exceeded. After 3 hours, the mixture is stirred with dilute hydrochloric acid and the crystalline reaction product is filtered off, washed until neutral and dried.

Yield 28.0 g; melting point: 98°–100° C.

2,6-Diethyl-phenyl isothiocyanate can be prepared as follows: 100 g of 2,6-diethylaniline in 200 ml of methylene chloride are added dropwise at 0°–5°, whilst stirring, to a mixture of 500 ml of methylene chloride, 300 ml of water, 120 g of calcium carbonate and 92 g of thiophosgene. The mixture is then heated to the reflux temperature until the evolution of $CO_2$ has ended. The cooled batch is filtered and the methylene chloride layer is separated off, dried with calcium chloride and fractionated.

Yield 112 g; boiling point 101°–103° C./1.4 mm Hg.

EXAMPLE 12

If, in the preceding example, the tert.-butylamine is replaced by the same amount of tert.-pentylamine and the procedure described is followed, N-(2,6-diethyl-phenyl)-N'-tert.-pentyl-thiourea, melting point: 85°–87° C., is obtained.

EXAMPLE 13

N-(2,6-Di-sec.-butyl-phenyl)-N'-isopropyl-thiourea 15.0 g of 2,6-di-sec.-butyl-phenyl isothiocyanate are introduced, whilst cooling, into 20 g of a 65% strength aqueous solution of isopropylamine. After stirring for 3 hours at 20°, the batch is stirred into dilute hydrochloric acid, the reaction product which has precipitated in a crystalline form is filtered off and washed until neutral, and the paste is triturated with 50% strength methanol, again filtered off and dried.

Yield 17.0 g; melting point: 108°–111°.

EXAMPLE 14

If, in the above example, the isopropylamine is replaced by 15.0 g of sec.-butylamine and the procedure described is followed, N-(2,6-di-sec.-butyl-phenyl)-N'-sec.-butyl-thiourea is obtained; melting point: 103°–105° C.

EXAMPLE 15

Reaction of 2,6-diethyl-phenyl isothiocyanate with isopropylamine in accordance with the process described above gives N-(2,6-diethyl-phenyl)-N'-isopropyl-thiourea of melting point: 108° to 110°.

EXAMPLE 16

Substitution of iso-propylamine in Example 15 with sec.-butylamine gives N-(2,6-diethyl-phenyl)-N'-sec.-butyl-thiourea of melting point: 78°/80° C. is obtained.

EXAMPLE 17

N-(2-Methyl-6-ethyl-phenyl)-N'-tert.-pentyl-thioureas 15.0 g of 2-methyl-6-ethyl-phenyl isothiocyanate are introduced into 20.0 g of tert.-pentylamine whilst cooling. After 2 hours, the batch is stirred into dilute hydrochloric acid and the reaction product is filtered off, triturated with 50% strength methanol, filtered off and dried.

Yield 19.0 g; melting point: 78°–81° C. 2-Methyl-6-ethyl-phenyl isothiocyanate can be prepared as follows: 100 g of 2-methyl-6-ethyl-aniline in 200 ml of methylene chloride are added dropwise at 0°–5° to a mixture of 500 ml of methylene chloride, 300 ml of water, 120 g of calcium carbonate and 103 g of thiophosgene. The mixture is then heated under reflux until the evolution of $CO_2$ has ended. The solids are then filtered off and the methylene chloride layer is separated off, dried over calcium chloride and fractionated.

Yield 121 g; melting point; 88°–91° C./1.0 mm Hg.

EXAMPLE 18

If, in Example 17, the tert.pentylamine is replaced by the same amount of tert.-butylamine, N-(2-methyl-6-ethyl-phenyl)-N'-tert.-butyl-thiourea is obtained; melting point: 94°–96° C.

EXAMPLE 19

N-(4-Methyl-2,6-diethyl-phenyl)-N'-tert.-butyl-thiourea 15.0 g of 4-methyl-2,6-diethyl-phenyl isothiocyanate are introduced into 20.0 g of tert.-butylamine whilst cooling. The mixture is stirred for 2 hours and is poured into dilute hydrochloric acid and the product is filtered off, washed and dried.

Yield 18.0 g; melting point: 121°–123° C.

4-Methyl-2,6-diethyl-phenyl isothiocyanate, used above as the starting compound, can be prepared as follows: 100 g of 2,4-dimethyl-6-ethyl-aniline in 200 ml of methylene chloride are added dropwise at 0°–56° whilst stirring, to a mixture of 500 ml of methylene chloride, 300 ml of water, 120 g of calcium carbonate and 92 g of thiophosgene. The mixture is then heated to the reflux temperature until the evolution of $CO_2$ has ended. After it has cooled, the batch is filtered to remove solids and the methylene chloride layer is separated off, dried over calcium chloride and fractionated; yield 118 g, boiling point 101°–104° C./1.5 mm Hg.

Using the same process, 4-methyl-2,6-diethylaniline and thiophosgene give 4-methyl-2,6-diethyl-phenyl isothiocyanate, boiling point 113°–116° C./1.2 mm Hg.

EXAMPLE 20

If, in Example 19, the tert.-butylamine is replaced by the same amount of tert.-pentylamine and the same procedure described is followed, N-(4-methyl-2,6-diethyl-phenyl)-N'-tert.-pentyl-thiourea, melting point: 98°–101° C., is obtained.

EXAMPLE 21

Analogously to Example 20, 2,4-dimethyl-6-ethyl-phenyl isothiocyanate and tert.-butylamine give N-(2,4-dimethyl-6-ethyl-phenyl)-N'-tert.-butyl-thiourea, melting point: 130°–132° C.

EXAMPLE 22

The substituted phenyl isothiocyanate used in Example 20 and tert.-pentylamine give N-(2,4-dimethyl-6-ethyl-phenyl)-N'-tert.-pentyl-thiourea, melting point: 105°–107° C.

EXAMPLE 23

4-Cyclohexyl-2,6-diethyl-phenyl isothiocyanate 231 g of 4-cyclohexyl-2,6-diethyl-aniline in 300 ml of methylene chloride are added dropwise at 10°–15° C. to a suspension of 600 ml of methylene chloride, 500 ml of water, 200 g of calcium carbonate and 140 g of thiophosgene. The mixture is then heated to the boil, until the evolution of gas has ended. The batch, when cold, is filtered to remove solids, and the methylene chloride layer is dried over calcium chloride and fractionated; boiling point 175°–179° C./1.5 mm Hg; yield 251 g.

EXAMPLES 24 TO 43

The following aryl isothiocyanates can be prepared analogously to Example 22, from the corresponding aniline derivatives. Example 24: 2,4,6-triethyl-phenyl isothiocyanate boiling point 128°–130° C./1.3 mm Hg. Example 25: 4-n-propyl-2,6-diethyl-phenyl isothiocyanate, boiling point 132°–137° C./1.5 mm Hg. Example 26: 4-isopropyl-2,6-diethyl-phenyl isothiocyanate, boiling point 130°–132° C./1.3 mm Hg. Example 27: 4-n-butyl-2,6-diethyl-phenyl isothiocyanate, boiling point 150°–155° C./2.0 mm Hg. Example 28: 4-isobutyl-2,6-diethyl-phenyl isothiocyanate, boiling point 133°–136° C./1.4 mm Hg. Example 29: 4-tert.-butyl-2,6-diethyl-phenyl isothiocyanate, boiling point 130°–133° C./1.8 mm Hg. Example 30: 2,6-di-cyclopentyl-phenyl isothiocyanate, boiling point 165°–158° C./1.3 mm Hg. Example 31: 4-methyl-2,6-dicyclophentylphenyl isothiocyanate, boiling point 188°–195° C./2.0 mm Hg. Example 32: 2,6-di-pent-2-yl-phenyl isothiocyanate, boiling point 148°–152° C./1.4 mm Hg. Example 33: 4-methyl-2,6-di-sec.-butyl-phenyl isothiocyanate, boiling point 130°–132° C./1.2 mm Hg. Example 34: 2-methyl-4,6-di-tert.-butyl-phenyl isothiocyanate, boiling point 135°–139° C./1.5 mm Hg. Example 35: 3-methyl-2,6-diethyl-phenyl isothiocyanate, boiling point 110°–113° C./1.0 mm Hg. Example 36: 3-chloro-2,6-diethyl-phenyl isothiocyanate, boiling point 118°–121° C./1.2 mm Hg. Example 37: 3,4-dimethyl-2,6-diethyl-phenyl isothiocyanate, boiling point 125°–130° C./1.2 mm Hg. Example 38: 3,5-dimethyl-2,6-diethyl-phenyl isothiocyanate, boiling point 119°–127° C./1.0 mm Hg. Example 39: 4-methyl-2-ethyl-6-sec.-butyl-phenyl isothiocyanate, boiling point 126°–128° C./1.5 mm Hg. Example 40: 4-methyl-2,6-diisopropyl-phenyl isothiocyanate, boiling point 124°–126° C./1.2 mm Hg. Example 41: 2-isopropyl-6-sec.-butyl-phenyl isothiocyanate, boiling point 115°–117° C./1.0 mm Hg. Example 42: 2,4,6-tri-isopropyl-phenyl isothiocyanate, boiling point 130°–132° C./1.2 mm Hg. Example 43: 2-ethyl-6-isopropyl-phenyl isothiocyanate, boiling point 104°–106° C./1.2 mm Hg.

The 2,6-disubstituted aniline derivatives required as the starting material for the synthesis of these aryl isothiocyanates can be prepared in accordance with the process described in Angew. Chemie, volume 69, page 124 et seq. (1975).

EXAMPLE 44

4-Cyclohexyl-2,6-diethyl-aniline

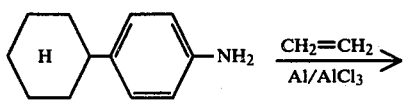

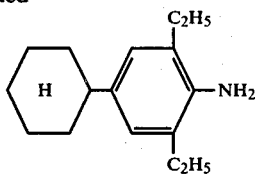

300 g of 4-amino-cyclohexylbenzene, 5.0 g of aluminium granules and 17 g of anhydrous aluminium chloride are heated in a steel autoclave to 250° C. and ethylene is injected until the internal pressure is 200 atomspheres gauge. After the pressure has dropped, further ethylene is pumped in until the absorption has ended; duration, about 7 hours. After it has cooled, the batch, is stirred with 500 ml of benzene, 300 ml of 40% strength sodium hydroxide solution and 500 ml of water for 15 minutes at 40°–50° C. and the benzene phase is separated off, washed with water, dried over potassium carbonate and fractionated. Boiling point 148°–150° C./0.8 mm Hg; yield 318 g.

EXAMPLES 45 TO 57

The following aniline derivatives can be prepared analogously to Example 44.

Example 45: 2,4,6-triethyl-aniline, boiling point 89°–91° C./0.6 mm Hg. Example 46: 4-n-propul-2,6-diethyl-aniline, boiling point 102° C./1.4 mm Hg. Example 47: 4-isopropyl-2,6-diethyl-aniline, boiling point 103°–105° C./2.0 mm Hg. Example 48: 4-n-butyl-2,6-diethyl-aniline, boiling point 117°–118° C./2.0 mm Hg. Example 49: 4-isobutyl-2,6-diethyl-aniline, boiling point 97°–99° C./0.7 mm Hg. Example 50: 4-tert.-butyl-2,6-diethyl-aniline, boiling point 89°–91° C./0.6 mm Hg. Example 51: 2-ethyl-6-isopropyl-aniline, boiling point 127°–128° C./16 mm Hg. Example 52: 2-isopropyl-6-sec.-butyl-aniline, boiling point 136°–143° C./13 mm Hg. Example 53: 3-methyl-2,6-diethyl-aniline, boiling point 132°–133° C./20 mm Hg. Example 54: 3-chloro-2,6-diethyl-aniline, boiling point 145°–148° C./15 mm Hg. Example 55: 3,4-dimethyl-2,6-diethyl-aniline, boiling point 147°–148° C./15 mm Hg. Example 56: 3,5-dimethyl-2,6-dimethyl-aniline, boiling point 146°–154° C./15 mm Hg, melting point 47°–50° C. Example 57: 4-methyl-2,6-diisopropyl-aniline, boiling point 141°–143° C./16 mm Hg.

EXAMPLE 58

2,6-Bis-(pent-2-yl)-aniline

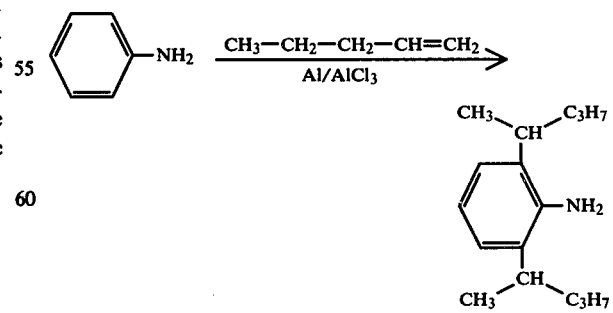

170 g of aniline, 5 g of aluminium granules and 15 g of anhydrous aluminium chloride are heated in a steel autoclave to 300° C. and 300 g of pent-1-ene are pumped in over the course of about 5 hours, until the internal pressure is 300 atmospheres gauge. The batch is then kept at 300° C. for a further 6 hours, in the course of which the internal pressure drops to 107 atmospheres gauge. After it has cooled, the content of the autoclave is stirred with 500 ml of benzene, 250 ml of 40% strength sodium hydroxide solution and 300 ml of water for 15 minutes at 30°–40° C. and the benzene layer is washed with water, dried over potassium carbonate and fractionated. 113 g of 2-mono-pent-2-yl-aniline, boiling point 78°–82° C./0.6 mm Hg, and 131 g of 2,6-bis-pent-2-yl-aniline, boiling point 168°–174° C./1.5 mm Hg are obtained.

EXAMPLES 59 TO 61

Analogously to Example 58, the following compounds can be obtained: Example 59, aniline and cyclopentene give 2-cyclopentyl-aniline, boiling point 102°–109° C./1.7 mm Hg, and 2,6-di-cyclopentyl-aniline, boiling point 159°–165° C./1.5 mm Hg. Example 60: p-toluidine and cyclopentene give 4-methyl-2-cyclopentyl-aniline, boiling point 104°–106° C./0.7 mm Hg and 4-methyl-2,6-dicyclopentyl-aniline, boiling point 157°–158° C./0.8 mm Hg. Example 61: p-toluidine and but-1-ene give 4-methyl-2-sec,-butyl-aniline, boiling point 72° C./1.0 mm Hg and 4-methyl-2,6-di-sec.-butyl-aniline, boiling point 121°–128° C./3.0 mm Hg.

EXAMPLES 62 AND 63

Analogously to Example 58, the following compounds can be obtained. Example 62: aniline and but-1-ene give 2-sec.-butyl-aniline, boiling point 109°–111° C./13 mm Hg and 2,6-di-sec.-butyl-aniline, boiling point 145°–147° C./13 mm Hg. Example 63: o-Toluidine and isobutene, with Tonsil K 10 as the catalyst, at 200° C. and 200 atmospheres gauge give 6-methyl-2,4-di-tert,-butyl-aniline, boiling point 101°–103° C./1.1 mm Hg.

EXAMPLES 64 TO 215

The following active compounds are obtained analogously to Examples 1, 7, 9, 11, 13, 17 or 19, from the corresponding 2,6-disubstituted phenyl isothiocyanates and alkylamines.

Table $$Ar-NH-\overset{\underset{\Vert}{S}}{C}-NH-Alk$$

| Example No. | Ar | Alk | Melting point: [°C.] |
|---|---|---|---|
| 64 | 2,6-di-$C_2H_5$-phenyl | $-CH(CH_3)-CH_2-CH_2-CH_3$ | 84–86 |
| 65 | " | $-CH(CH_2-CH_3)_2$ | 103–104 |
| 66 | " | $-CH(CH_3)-C(CH_3)_2-CH_3$ | 109–111 |
| 67 | 4-$CH_3$-2,6-di-$C_2H_5$-phenyl | $-CH(CH_3)_2$ | 143–145 |
| 68 | " | $-CH(CH_3)-CH_2-CH_3$ | 119–120 |
| 69 | " | $-C(C_2H_5)_2-CH_3$ | 98–100 |
| 70 | " | $-C(C_2H_5)_3$ | 110–112 |
| 71 | " | $-CH(CH_3)-CH_2-CH_2-CH_3$ | 70–72 |
| 72 | " | $-CH(CH_3)-C(CH_3)_2-CH_3$ | 120–123 |
| 73 | " | $-CH(CH_3)-CH_2-CH(CH_3)-CH_3$ | 124–126 |

Table-continued $$Ar-NH-\overset{\overset{S}{\|}}{C}-NH-Alk$$

| Example No. | Ar | Alk | Melting point: [°C] |
|---|---|---|---|
| 74 | 2-C₂H₅, 6-CH₃, 4-C₂H₅-phenyl | -C(CH₃)₃ | 119–120 |
| 75 | " | -C(CH₃)₂-C₂H₅ | 115–117 |
| 76 | " | -CH(CH₃)-CH₂-CH₂-CH₃ | 123–125 |
| 77 | " | -CH(CH₃)-C(CH₃)₂-CH₃ | 112–115 |
| 78 | 2-C₂H₅, 6-Cl, 4-C₂H₅-phenyl | -C(CH₃)₃ | 108–110 |
| 79 | " | -C(CH₃)(C₂H₅)CH₃ | 95–97 |
| 80 | " | -CH(CH₃)-CH₂-CH₃ | 99–102 |
| 81 | 2-C₂H₅, 3,6-(CH₃)₂, 4-C₂H₅-phenyl | -CH(CH₃)₂ | 168–169 |
| 82 | " | -CH(CH₃)-CH₂-CH₃ | 150–151 |
| 83 | " | -C(CH₃)₃ | 144–145 (decomposition) |
| 84 | " | -C(CH₃)₂-C₂H₅ | 133–136 |
| 85 | 2-C₂H₅, 3,5-(CH₃)₂, 4-C₂H₅-phenyl | -CH(CH₃)₂ | 152–155 |
| 86 | " | -CH(CH₃)-CH₂-CH₃ | 128–130 |
| 87 | " | -C(CH₃)₃ | 138–140 (decomposition) |
| 88 | " | -C(CH₃)₂-C₂H₅ | 130–132 |

Table-continued $$Ar-NH-\overset{\overset{S}{\|}}{C}-NH-Alk$$

| Example No. | Ar | Alk | Melting point: [°C.] |
|---|---|---|---|
| 89 | " | $-CH(CH_3)-C(CH_3)_2-CH_3$ | 151–154 |
| 90 | 2-C$_2$H$_5$, 3-CH(CH$_3$)$_2$-phenyl | $-CH(CH_3)_2$ | 89–90 |
| 91 | " | $-CH(CH_3)-CH_2-CH_3$ | 85–87 |
| 92 | " | $-C(CH_3)_2-CH_3$ (with extra CH$_3$) $-C(CH_3)_3$ | 113–115 |
| 93 | " | $-C(CH_3)(C_2H_5)-CH_3$ | 97–98 |
| 94 | " | $-CH(CH_2CH_3)_2$ | 113–115 |
| 95 | " | $-CH(CH_3)-C(CH_3)_2-CH_3$ | 127–128 |
| 96 | 2-C$_2$H$_5$, 5-CH$_3$, 4-CH(CH$_3$)$_2$-phenyl | $-C(CH_3)_3$ | 104–107 |
| 97 | " | $-C(CH_3)_2-C_2H_5$ | 96–97 |
| 98 | 2,6-di[CH(CH$_3$)$_2$]-phenyl | $-CH(CH_3)-CH_2-CH_3$ | 108–112 |
| 99 | " | $-C(C_2H_5)_2-CH_3$ | 129–131 |
| 100 | " | $-C(C_2H_5)_3$ | 139–141 |
| 101 | " | $-CH(CH_3)-CH_2-CH_2-CH_3$ | 90–92 |

Table-continued $$Ar-NH-\overset{\overset{S}{\|}}{C}-NH-Alk$$

| Example No. | Ar | Alk | Melting point: [°C.] |
|---|---|---|---|
| 102 | " | -CH(CH₂-CH₃)(CH₂-CH₃) | 101-105 |
| 103 | " | -CH(CH₃)-CH(CH₃)-CH₃ | 128-131 |
| 104 | " | -CH(CH₃)-C(CH₃)(CH₃)-CH₃ | 152-156 |
| 105 | 2,4,6-tri(isopropyl)phenyl (with CH₃ at 3,5 position as shown: ring with three -CH(CH₃)₂ groups and a CH₃) | -CH(CH₃)(CH₃) | 192-193 (decomposition) |
| 106 | " | -C(CH₃)(CH₃)-CH₃ | 152-153 (decomposition) |
| 107 | " | -C(CH₃)(C₂H₅)-CH₃ | 153-154 (decomposition) |
| 108 | " | -CH(CH₃)-CH₂-CH₃ | 175-178 |
| 109 | " | -CH(CH₃)-CH₂-CH₂-CH₃ | 125-128 |
| 110 | " | -CH(CH₂-CH₃)(CH₂-CH₃) | 170-172 |
| 111 | " | -CH(CH₃)-C(CH₃)(CH₃)-CH₃ | 185-187 |
| 112 | 2,6-di-substituted phenyl: one -CH(CH₃)₂ and one -CH(CH₃)(C₂H₅) | -CH(CH₃)-CH₂-CH₃ | 88-92 |
| 113 | " | -CH(CH₃)-CH₂-CH₂-CH₃ | 81 |
| 114 | 2,4,6-tri[CH(CH₃)₂]phenyl | -CH(CH₃)(CH₃) | 133-135 |

Table-continued $$Ar-NH-\overset{\overset{S}{\|}}{C}-NH-Alk$$

| Example No. | Ar | Alk | Melting point: [°C.] |
|---|---|---|---|
| 115 | " | –CH(CH₃)–CH₂–CH₃ | 120–122 |
| 116 | " | –C(CH₃)₂–CH₃ | 133–135 |
| 117 | " | –C(CH₃)(C₂H₅)–CH₃ | 115–118 |
| 118 | " | –CH(CH₃)–CH₂–CH₂–CH₃ | 120–123 |
| 119 | 2,4,6-triisopropylphenyl | –CH(CH₃)–C(CH₃)₂–CH₃ | 155–158 |
| 120 | 2,4,6-tri(sec-butyl)phenyl [CH₃–CH(C₂H₅)–] | –CH(CH₃)–CH₂–CH₂–CH₃ | oil |
| 121 | " | –CH₂–CH(CH₃)–CH₃ | 83–85 |
| 122 | " | –CH(CH₃)–C(CH₃)₂–CH₃ | 96–100 |
| 123 | " | –CH(CH₂–CH₃)₂ | 89–96 |
| 124 | " | –C(C₂H₅)₂–CH₃ | 93–96 |
| 125 | 2,4,6-tri(sec-butyl)phenyl [CH₃–CH(C₂H₅)–, CH₃ at 4] | –C(CH₃)₂–CH₃ | 130–132 |
| 126 | " | –C(CH₃)(C₂H₅)–CH₃ | 120–123 |
| 127 | " | –CH(CH₃)–CH₂–CH₃ | 119–123 |
| 128 | " | –CH(C₂H₅)₂ | 115–117 |

Table-continued
$$Ar-NH-\overset{\overset{S}{\|}}{C}-NH-Alk$$
| Example No. | Ar | Alk | Melting point: [°C.] |
|---|---|---|---|
| 129 | 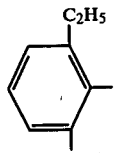 2,6-(C₂H₅)₂-C₆H₃ | 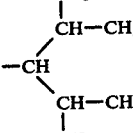 -CH(CH(CH₃)₂)₂ | 103–106 |
| 130 | 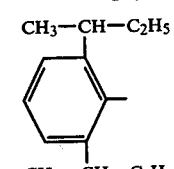 2,4-(CH₃CHC₂H₅)₂-C₆H₃ | " | 102–105 |
| 131 | 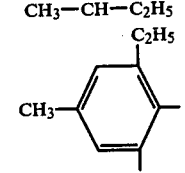 2,6-(C₂H₅)₂-4-CH₃-C₆H₂ (with extra C₂H₅) | 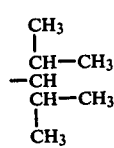 -CH(CH(CH₃)₂)₂ | 116–118 |
| 132 | 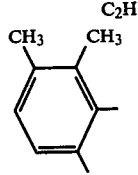 2,3-(CH₃)₂-4-C₂H₅-C₆H₃ | " | 118–120 |
| 133 | 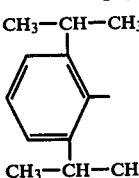 2,4-(iPr)₂-C₆H₄ | " | 146–148 |
| 134 | 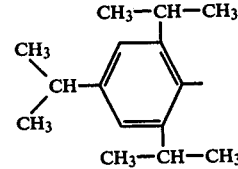 2,4,6-(iPr)₃-C₆H₂ | " | 155–160 |
| 135 | 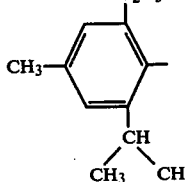 | " | 78–87 |
| 136 | 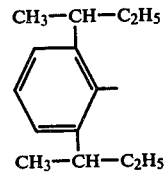 2,4-(CH₃CHC₂H₅)₂-C₆H₃ | 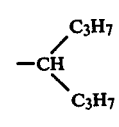 -CH(C₃H₇)₂ | 70–73 |
| 137 | 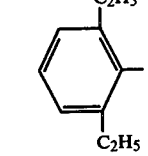 2,6-(C₂H₅)₂-C₆H₃ | " | 102–105 |

Table-continued $$Ar-NH-\overset{\overset{S}{\|}}{C}-NH-Alk$$

| Example No. | Ar | Alk | Melting point: [°C.] |
|---|---|---|---|
| 138 | 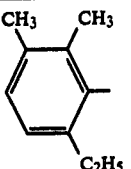 | 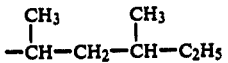 | oil |
| 139 | 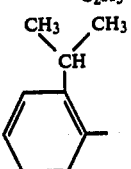 | " | oil |
| 140 | 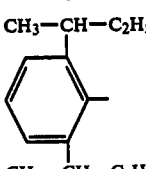 | " | oil |
| 141 | 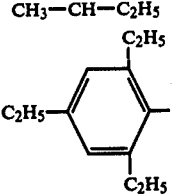 | $-\overset{CH_3}{\underset{}{CH}}-CH_2-CH_2-CH_3$ | 70–72 |
| 142 | " | $-\overset{CH_3}{\underset{}{CH}}-CH_2-CH_3$ | 97–99 |
| 143 | " | $-\overset{CH_3}{\underset{CH_3}{\overset{|}{C}}}-CH_3$ | 78–80 |
| 144 | " | $-\overset{CH_3}{\underset{CH_3}{\overset{|}{C}}}-C_2H_5$ | 88–90 |
| 145 | 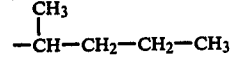 | $-\overset{CH_3}{\underset{}{CH}}-CH_2-CH_2-CH_3$ | 117–119 |
| 146 | " | $-\overset{CH_3}{\underset{}{CH}}-CH_2-CH_3$ | 148–152 |
| 147 | " | $-\overset{CH_3}{\underset{CH_3}{\overset{|}{C}}}-CH_3$ | 128–135 (decompositon) |
| 148 | " | $-\overset{CH_3}{\underset{CH_3}{\overset{|}{C}}}-C_2H_5$ | 135–140 (decomposition) |

Table-continued $$Ar-NH-\overset{\overset{S}{\|}}{C}-NH-Alk$$

| Example No. | Ar | Alk | Melting point: [°C.] |
|---|---|---|---|
| 149 | ![Ar1: 2,4-di-C2H5-5-tert-butyl-phenyl with CH3 substituent] | $-\overset{CH_3}{\underset{}{CH}}-CH_2-CH_2-CH_3$ | 100–102 |
| 150 | " | $-\overset{CH_3}{\underset{}{CH}}-CH_2-CH_3$ | 113–114 |
| 151 | " | $-\overset{CH_3}{\underset{CH_3}{\overset{|}{C}}}-CH_3$ | 153 (decomposition) |
| 152 | " | $-\overset{CH_3}{\underset{CH_3}{\overset{|}{C}}}-C_2H_5$ | 129–130 |
| 153 | " | $-\overset{CH_3}{\underset{CH_3}{\overset{|}{C}}}-CH_2-\overset{CH_3}{\underset{}{CH}}-CH_3$ | 163–165 |
| 154 | " | $-CH\begin{smallmatrix}CH-CH_3\\|\\CH_3\\\\CH-CH_3\\|\\CH_3\end{smallmatrix}$ | 134–136 |
| 155 | " | $-CH\begin{smallmatrix}C_2H_5\\\\C_2H_5\end{smallmatrix}$ | 125–126 |
| 156 | ![Ar2: 2,4-di-C2H5-5-isobutyl-phenyl with CH3 substituent] | $-\overset{CH_3}{\underset{}{CH}}-CH_2-CH_2-CH_3$ | oil |
| 157 | " | $-\overset{CH_3}{\underset{}{CH}}-CH_2-CH_3$ | 64–66 |
| 158 | " | $-\overset{CH_3}{\underset{CH_3}{\overset{|}{C}}}-CH_3$ | 74–76 |
| 159 | " | $-\overset{CH_3}{\underset{CH_3}{\overset{|}{C}}}-C_2H_5$ | 73–74 |
| 160 | " | $-CH\begin{smallmatrix}C_2H_5\\\\C_2H_5\end{smallmatrix}$ | 84–86 |
| 161 | " | $-\overset{CH_3}{\underset{}{CH}}-\overset{CH_3}{\underset{CH_3}{\overset{|}{C}}}-CH_3$ | 100–103 |
| 162 | " | $-CH\begin{smallmatrix}CH_3\\\\CH_3\end{smallmatrix}$ | oil |
| 163 | " | $-\overset{CH_3}{\underset{}{CH}}-\overset{CH_3}{\underset{}{CH}}-CH_3$ | oil |

Table-continued

Ar—NH—C(=S)—NH—Alk

| Example No. | Ar | Alk | Melting point: [°C.] |
|---|---|---|---|
| 164 | 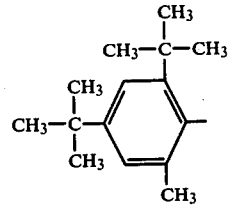 | $-\underset{\underset{CH_3}{\mid}}{CH}-CH_2-CH_2-CH_3$ | 132–134 |
| 165 | " | $-\underset{\underset{CH_3}{\mid}}{CH}-CH_2-CH_3$ | 137–139 |
| 166 | " | $-\underset{\underset{CH_3}{\mid}}{\overset{\overset{CH_3}{\mid}}{C}}-C_2H_5$ | 140–143 |
| 167 | " | $-\underset{\underset{CH_3}{\mid}}{\overset{\overset{CH_3}{\mid}}{C}}-CH_3$ | 156 (decomposition) |
| 168 | 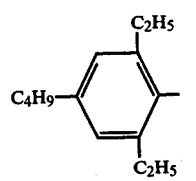 | $-\underset{\underset{CH_3}{\mid}}{CH}-CH_2-CH_2-CH_3$ | oil |
| 169 | " | $-\underset{\underset{CH_3}{\mid}}{CH}-CH_2-CH_3$ | oil |
| 170 | " | $-\underset{\underset{CH_3}{\mid}}{\overset{\overset{CH_3}{\mid}}{C}}-CH_3$ | 82–84 |
| 171 | " | $-\underset{\underset{CH_3}{\mid}}{\overset{\overset{CH_3}{\mid}}{C}}-C_2H_5$ | 52–54 |
| 172 | " | $-\underset{\underset{C_2H_5}{\mid}}{CH}-C_4H_9$ | oil |
| 173 | 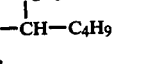 | $-\underset{\underset{CH_3}{\mid}}{CH}-CH_2-CH_2-CH_3$ | 137–139 |
| 174 | " | $-\underset{\underset{CH_3}{\mid}}{CH}-CH_2-CH_3$ | 186–189 |
| 175 | " | $-\underset{\underset{CH_3}{\mid}}{\overset{\overset{CH_3}{\mid}}{C}}-CH_3$ | 168–170 (decomposition) |
| 176 | " | $-\underset{\underset{CH_3}{\mid}}{\overset{\overset{CH_3}{\mid}}{C}}-C_2H_5$ | 152 (decomposition) |

Table-continued $$Ar-NH-\overset{\underset{\|}{S}}{C}-NH-Alk$$

| Example No. | Ar | Alk | Melting point: [°C.] |
|---|---|---|---|
| 177 | 2,5-diethyl-4-methyl-... (C₂H₅, C₃H₇, C₂H₅ substituted phenyl) | $-CH(CH_3)-CH_2-CH_2-CH_3$ | oil |
| 178 | " | $-CH(CH_3)-CH_2-CH_3$ | oil |
| 179 | " | $-C(CH_3)_2-CH_3$ | oil |
| 180 | " | $-C(CH_3)(CH_3)-C_2H_5$ | oil |
| 181 | " | $-CH(CH_3)-C(CH_3)_2-CH_3$ | oil |
| 182 | " | $-CH(C_2H_5)_2$ | oil |
| 183 | " | $-CH(CH_3)-CH(CH_3)-CH_3$ | oil |
| 184 | cyclohexyl-(2,5-diethyl-4-methyl)phenyl (Ar with H on cyclohexyl) | $-CH(CH_3)-CH_2-CH_2-CH_3$ | 93–95 |
| 185 | " | $-CH(CH_3)-CH_2-CH_3$ | 120–124 |
| 186 | " | $-C(CH_3)_2-CH_3$ | 110–112 |
| 187 | " | $-C(CH_3)(CH_3)-C_2H_5$ | 115–118 |
| 188 | " | $-CH(C_2H_5)_2$ | 142–144 |
| 189 | " | $-CH(CH_3)-CH(CH_3)-CH_3$ | 138–140 |
| 190 | 2,6-bis(1-methylbutyl...)phenyl with CH(CH₃)(C₃H₇) groups | $-CH(CH_3)-CH_2-CH_2-CH_3$ | oil |
| 191 | " | $-CH(CH_3)-CH_2-CH_3$ | oil |

Table-continued $$Ar-NH-\overset{\overset{S}{\|}}{C}-NH-Alk$$

| Example No. | Ar | Alk | Melting point: [°C.] |
|---|---|---|---|
| 192 | " | −CH(C$_2$H$_5$)$_2$ (−CH with two C$_2$H$_5$) | oil |
| 193 | " | −C(CH$_3$)$_3$ | oil |
| 194 | " | −C(CH$_3$)$_2$C$_2$H$_5$ | oil |
| 195 | 2,6-bis(sec-butyl)phenyl [CH(CH$_3$)(C$_2$H$_5$)]$_2$-phenyl | −CH(CH$_3$)CH(CH$_3$)−CH$_3$ | oil |
| 196 | " | −CH(CH$_3$)−CH$_2$−CH(CH$_3$)−CH$_3$ | oil |
| 197 | " | −CH(CH$_3$)−C(CH$_3$)$_2$−CH$_3$ | 100–103 |
| 198 | 2,6-diethylphenyl | −CH(C$_2$H$_5$)−C$_4$H$_9$ | 72–75 |
| 199 | 2,6-bis(isopropyl)phenyl | " | 102–104 |
| 200 | 2,4,6-triethylphenyl | " | oil |
| 201 | 2,6-bis(sec-butyl)phenyl | " | oil |

Table-continued $$Ar-NH-\underset{\underset{S}{\|}}{C}-NH-Alk$$

| Example No. | Ar | Alk | Melting point: [°C.] |
|---|---|---|---|
| 202 | 2,5-di-C$_2$H$_5$, 4-C$_2$H$_5$-phenyl (C$_2$H$_5$, C$_2$H$_5$, C$_2$H$_5$ substituted phenyl) | $-C(CH_3)(C_2H_5)(C_3H_7)$ | oil |
| 203 | " | $-CH(CH_3)-CH_2-CH(CH_3)-C_2H_5$ | oil |
| 204 | 2-C$_2$H$_5$, 5-CH$_3$, 4-C$_2$H$_5$ phenyl | " | oil |
| 205 | 2,6-di-C$_2$H$_5$, 4-cyclohexyl phenyl | " | 86–92 |
| 206 | 2,6-di-C$_2$H$_5$, 4-isopropyl phenyl | $-C(CH_3)_3$ | 117–118 |
| 207 | " | $-C(CH_3)_2-C_2H_5$ | 91–93 |
| 208 | " | $-CH_2-CH(CH_3)_2$ | 98–100 |
| 209 | " | $-CH(CH_3)-CH_2-CH_3$ | 123–125 |
| 210 | " | $-CH(CH_2-CH_3)_2$ | 112–115 |
| 211 | " | $-CH(CH_3)-CH_2-CH_2-CH_3$ | 67–70 |
| 212 | 2,5-di-C$_2$H$_5$, 4-C$_2$H$_5$ phenyl | $-CH(CH_3)-C_5H_{11}(n)$ | oil |
| 213 | 2-C$_2$H$_5$, 5-C$_3$H$_7$, 4-C$_2$H$_5$ phenyl | " | oil |

Table-continued $$Ar-NH-\underset{\underset{S}{\|}}{C}-NH-Alk$$

| Example No. | Ar | Alk | Melting point: [°C.] |
|---|---|---|---|
| 214 | 4-ethyl-2-isopropyl-5-ethyl-phenyl (see structure) | " | oil |
| 215 | 2-ethyl-4-butyl-5-ethyl-phenyl (see structure) | " | oil |

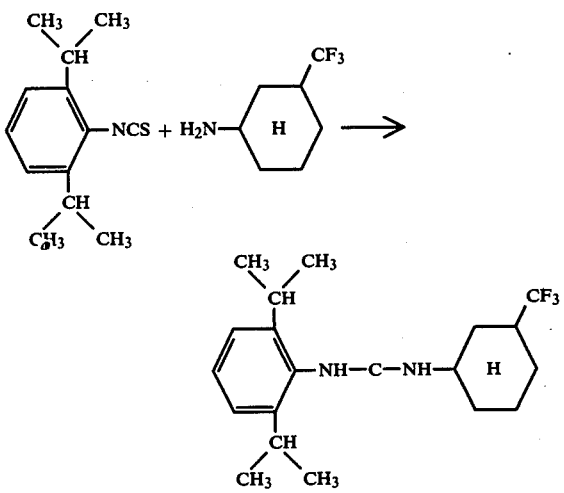

EXAMPLE 216

N-(2,6-Diisopropyl-phenyl)-N'-(3-trifluoromethyl-cyclohexyl)thiourea 16.0 g of 3-trifluoromethyl-cyclohexylamine are taken and 18.0 g of 2,6-diisopropyl-phenyl isothiocyanate are introduced whilst stirring. The reaction commences with slight evolution of heat. The mixture is left to stand for 12 hours and is then stirred with dilute hydrochloric acid. The crystalline product is filtered off, triturated with dilute methanol, filtered off and dried. The compound is obtained in the form of a stereomer mixture of melting point 67°–75° C.; yield 27 g. The elementary analysis and NMR and IR spectra agree with the assumed structure.

EXAMPLE 217

N-(2,6-Di-sec.-butyl-phenyl)-N'-cyclopentyl-thiourea

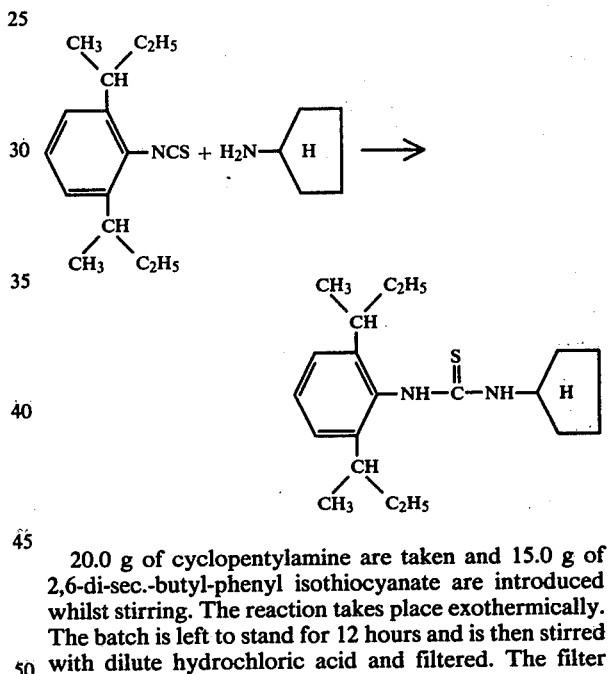

20.0 g of cyclopentylamine are taken and 15.0 g of 2,6-di-sec.-butyl-phenyl isothiocyanate are introduced whilst stirring. The reaction takes place exothermically. The batch is left to stand for 12 hours and is then stirred with dilute hydrochloric acid and filtered. The filter cake is triturated with dilute methanol, filtered off, washed and dried. For further purification, the product can be recrystallised from petroleum ether. Yield 18 g; melting point 107°–108° C.

The elementary analysis, and NMR and IR spectrum agree with the assumed structure.

EXAMPLE 218

N-(2,6-Di-sec.-butyl-phenyl)-N'-cyclohexylthiourea can be obtained analogously to Example 217 from cyclohexylamine and 2,6-di-sec.-butyl-phenyl isothiocyanate; melting point: 140° C.

EXAMPLE 219

N-(2,4,6-Triethyl-phenyl)-N'-cyclohexyl-thiourea

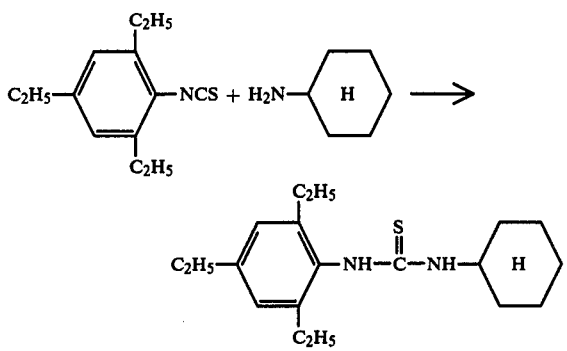

20.0 g of cyclohexylamine are taken and 15.0 g of 2,4,6-triethyl-phenyl isothiocyanate are introduced whilst stirring. The reaction takes place with slight evolution of heat. The mixture is left to stand for 12 hours and is then stirred with dilute hydrochloric acid and filtered. The crystalline reaction product is triturated with dilute methanol filtered off, washed and dried; yield 22.0 g; melting point 97°–99° C. The elementary analysis and NMR- and IR-spectrum agree with the assumed structure.

EXAMPLE 220

N-(4-n-Butyl-2,6-diethyl-phenyl)-N'-cyclohexyl-thiourea, in an oily form, is obtained analogously to Example 219 from cyclohexylamine and 4-n-butyl-2,6-diethyl-phenyl isothiocyanate.

What we claim is:

1. An N-aryl-N'-(cyclo)alkyl thiourea or an acid-addition salt thereof selected from the group consisting of N-(2,6-diisopropyl-phenyl)-N'-(3-trifluoromethylcyclohexyl)-thiourea, N-(2,6-di-sec.-butyl-phenyl)-N'-cyclopentyl-thiourea, N-(4-n-butyl-2,6-diethyl-phenyl)N'-cyclohexyl-thiourea.

2. A compound of claim 1 which is N-(2,6-diisopropylphenyl)-N'-(3-trifluoromethyl-cyclohexyl)-thiourea or an acid-addition salt thereof.

3. A compound of claim 1 which is N-(2,6-di-sec.-butylbutyl)-N'-cyclopentyl-thiourea or an acid-addition salt thereof.

4. A compound of claim 1 which is N-(4-n-butyl-2,6-diethyl-phenyl)-n'-cyclohexyl-thiourea or an acid-addition salt thereof.

5. A pesticidal composition containing a pesticidally effective amount of a compound for combatting a pest of the order Isopoda, Diplopoda, Chilopoda, Symphyla, Thysanura, Collembola, Orthoptera, Dermaptera, Isoptera, Anoplura, Mallophaga, Thysanoptera, Heteroptera, Homoptera, Lepidoptera, Coleoptera, Hymenoptera, Diptera, Siphonaptera, Arachnida or Acarina according to claim 1 in admixture with a solid or liquefied gaseous diluent or in admixture with a liquid diluent other than a solvent of a molecular weight less than 200 except in the presence of a surface-active agent.

6. A pesticidal composition containing a pesticidally effective amount of a compound for combatting a pest of the order Isopoda, Diplopoda, Chilopoda, Symphyla, Thysanura, Collembola, Orthoptera, Dermaptera, Isoptera, Anoplura, Mallophaga, Thysanoptera, Heteroptera, Homoptera, Lepidoptera, Coleoptera, Hymenoptera, Diptera Siphonaptera, Arachnida or Acarina according to claim 1 in the form of a sterile or isotonic aqueous solution.

7. A composition according to claim 6 containing from 0.5 to 95% by weight of the said compound.

8. A medicament in dosage unit form comprising a pesticidally effective amount of a compound for combatting a pest of the order Isopoda, Diplopoda, Chilopoda, Symphyla, Thysanura, Collembola, Orthoptera, Dermaptera, Isoptera, Anoplura, Mallophaga, Thysanoptera, Heteroptera, Homoptera, Lepidoptera, Coleoptera, Hymenoptera, Diptera, Siphonaptera, Arachnida or Acarina of claim 1 and an inert pharmaceutical carrier.

9. A medicament of claim 8 in the form of tablets, pills, dragees, capsules, ampoules, or suppositories.

10. A method of freeing or protecting domesticated animals from ectoparasites which comprises applying or administering to the animals an ectoparasiticidal amount of a compound of claim 1 alone or in admixture with a diluent or carrier, or in the form of a medicament.

11. A method of combatting animal and plant pests which comprises applying to the pests, or a habitat thereof a pesticidally effective amount of a compound for combatting a pest of the order isopoda, Diplopoda, Chilopoda, Symphyla, Thysanura, Collembola, Orthoptera, Dermaptera, Isoptera, Anoplura, Mallophaga, Thysanoptera, Heteroptera, Homoptera, Lepidoptera, Coleoptera, Hymenoptera, Diptera, Siphonaptera, Arachnida or Acarina according to claim 1 either alone or in admixture with a diluent or carrier.

12. A composition according to claim 5 containing from 0.5 to 95% by weight of the said compound.

* * * * *

UNITED STATES PATENT AND TRADEMARK OFFICE
CERTIFICATE OF CORRECTION

PATENT NO. : 4,194,008
DATED : March 18, 1980
INVENTOR(S) : Edgar Enders, et al.

It is certified that error appears in the above-identified patent and that said Letters Patent are hereby corrected as shown below:

Column 4, line 17, "arylaines" should be --arylamines--.
Column 4, line 29, "dimethy" should be --dimethyl--.
Column 5, line 14, "on" should be --can--.
Column 5, line 50, "cyclopentylamin e" should be --cyclopentylamine--.
Column 7, line 52, "2,6dicyclopentyl" should be --2,6-dicyclo...--.
Column 11, line 31, "Lithocollecties" should be --Lithocollectics--.

Column 25, B16, "$C_3H_5$" should be --$C_2H_5$--.
Column 27, C3, "$C_2H_5$" should be --$CH_3$--;"$C_3$ should be --$CH_3$--

UNITED STATES PATENT AND TRADEMARK OFFICE
CERTIFICATE OF CORRECTION

PATENT NO. : 4,194,008          Page 2 of 3
DATED     : March 18, 1980
INVENTOR(S) : Edgar Enders, et al.

It is certified that error appears in the above-identified patent and that said Letters Patent are hereby corrected as shown below:

Column 27, C5, "$CH_2H_5$" should be --$C_2H_5$--.

Column 29, C7, delete the formula and substitute the following formula

--  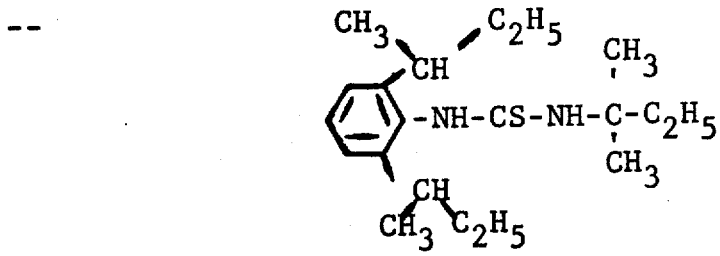

Column 35, D11, "(sec. 9" should be --(sec.)--.
Column 37, line 46, "butyl" 2nd occurr. should be -- Pentyl--.

UNITED STATES PATENT AND TRADEMARK OFFICE
CERTIFICATE OF CORRECTION

PATENT NO. : 4,194,008          Page 3 of 3
DATED : March 18, 1980
INVENTOR(S) : Edgar Enders, et al.

It is certified that error appears in the above-identified patent and that said Letters Patent are hereby corrected as shown below:

Column 70, line 43 "isopoda" should be --Isopoda--.

Signed and Sealed this

Fifteenth Day of July 1980

[SEAL]

Attest:

SIDNEY A. DIAMOND

Attesting Officer      Commissioner of Patents and Trademarks